(12) United States Patent
Benner et al.

(10) Patent No.: US 10,829,511 B1
(45) Date of Patent: *Nov. 10, 2020

(54) MOLECULAR RECOGNITION SYSTEMS WITH PYRIMIDINE ANALOG PAIRING

(71) Applicants: Steven A Benner, Gainesville, FL (US); Shuichi Hoshika, Gainesville, FL (US)

(72) Inventors: Steven A Benner, Gainesville, FL (US); Shuichi Hoshika, Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/530,600

(22) Filed: Aug. 2, 2019

Related U.S. Application Data

(63) Continuation-in-part of application No. 16/111,590, filed on Aug. 24, 2018, now Pat. No. 10,370,706, which is a continuation-in-part of application No. 15/461,073, filed on Mar. 16, 2017, now Pat. No. 10,059,737.

(51) Int. Cl.
*C07H 21/04* (2006.01)

(52) U.S. Cl.
CPC .................................. *C07H 21/04* (2013.01)

(58) Field of Classification Search
None
See application file for complete search history.

(56) References Cited

U.S. PATENT DOCUMENTS 10,059,737 B1 * 8/2018 Benner ............... C07H 21/04

* cited by examiner

*Primary Examiner* — Richard A Schnizer

(57) ABSTRACT

This invention covers oligonucleotide analogs that fold in part by having a segment of consecutive pyrimidine analogs form pyrimidine analog:pyrimidine analog pairs with another a segment of consecutive pyrimidine analogs segment, and where the segments pair by pyrimidine analog:pyrimidine analog "skinny" pairing. This pairing retains hydrogen bonding complementarity seen in standard DNA.

3 Claims, 10 Drawing Sheets

Figure 1:
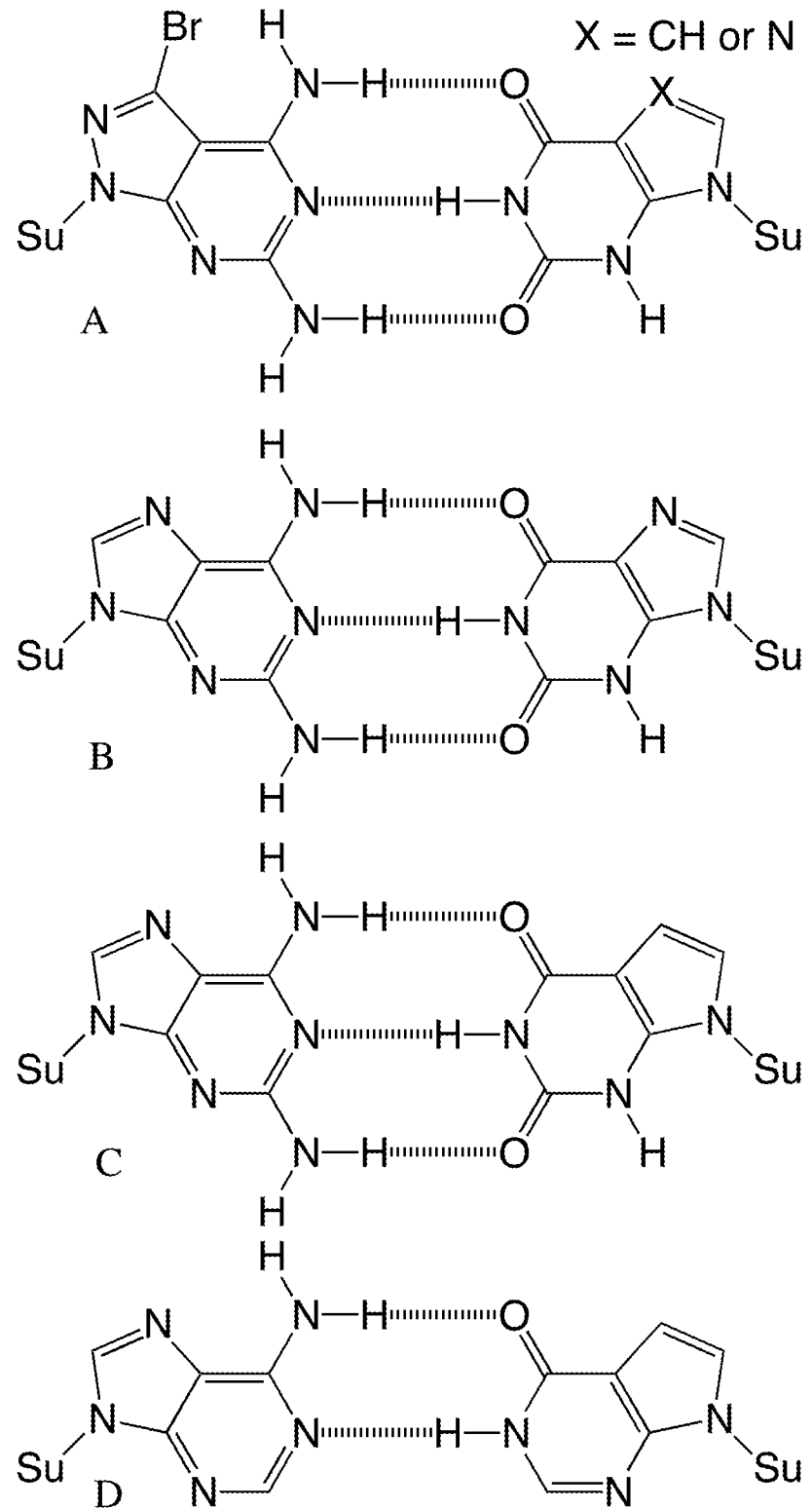

Specification includes a Sequence Listing.

SEQUENCE LISTING

<160> NUMBER OF SEQ ID NOS: 55

<210> SEQ ID NO 1
<211> LENGTH: 15
<212> TYPE: DNA
<213> ORGANISM: Artificial Sequence
<220> FEATURE:
<223> OTHER INFORMATION: Synthetic

<400> SEQUENCE: 1
cgtcgccccc ggctc                                                      15

<210> SEQ ID NO 2
<211> LENGTH: 15
<212> TYPE: DNA
<213> ORGANISM: Artificial Sequence
<220> FEATURE:
<223> OTHER INFORMATION: Synthetic

<400> SEQUENCE: 2
gagccggggg cgacg                                                      15

<210> SEQ ID NO 3
<211> LENGTH: 15
<212> TYPE: DNA
<213> ORGANISM: Artificial Sequence
<220> FEATURE:
<223> OTHER INFORMATION: Synthetic

<400> SEQUENCE: 3
cgtcgttttt ggctc                                                      15

<210> SEQ ID NO 4
<211> LENGTH: 15
<212> TYPE: DNA
<213> ORGANISM: Artificial Sequence
<220> FEATURE:
<223> OTHER INFORMATION: Synthetic

<400> SEQUENCE: 4
gagccaaaaa cgacg                                                      15

<210> SEQ ID NO 5
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 7-amino-9-(1'-beta-D-2'-deoxyribofuranosyl)-
      imidazo[1,2-c]pyrimidin-5(1H)-one

<400> SEQUENCE: 5
cgtcgttntt ggctc                                                      15

<210> SEQ ID NO 6
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 6-amino-3-(2'-deoxy-D-ribofuranosyl)-5-nitro-
      1H-pyridin-2-one

<400> SEQUENCE: 6
gagccaanaa cgacg                                                      15

<210> SEQ ID NO 7
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 7-amino-9-(1'-beta-D-2'-deoxyribofuranosyl)-
      imidazo[1,2-c]pyrimidin-5(1H)-one

<400> SEQUENCE: 7
cgtcgtnnnt ggctc                                                      15

<210> SEQ ID NO 8
<211> LENGTH: 15

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 6-amino-3-(2'-deoxy-D-ribofuranosyl)-5-nitro-
      1H-pyridin-2-one

<400> SEQUENCE: 8
gagccannna cgacg                                                       15

<210> SEQ ID NO 9
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (8)..(8)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (10)..(10)
<223> OTHER INFORMATION: 7-amino-9-(1'-beta-D-2'-deoxyribofuranosyl)-
      imidazo[1,2-c]pyrimidin-5(1H)-one

<400> SEQUENCE: 9
cgtcgntntn ggctc                                                       15

<210> SEQ ID NO 10
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (8)..(8)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (10)..(10)
<223> OTHER INFORMATION: 6-amino-3-(2'-deoxy-D-ribofuranosyl)-5-nitro-
      1H-pyridin-2-one

<400> SEQUENCE: 10
gagccnanan cgacg                                                       15

<210> SEQ ID NO 11
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 7-amino-9-(1'-beta-D-2'-deoxyribofuranosyl)-
```

-continued

```
    imidazo[1,2-c]pyrimidin-5(1H)-one

<400> SEQUENCE: 11
cgtcgnnnnn ggctc                                                    15

<210> SEQ ID NO 12
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 6-amino-3-(2'-deoxy-D-ribofuranosyl)-5-nitro-
      1H-pyridin-2-one

<400> SEQUENCE: 12
gagccnnnnn cgacg                                                    15

<210> SEQ ID NO 13
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 4-amino-N1-methyl-5-(1'-beta-D-2'-
      deoxyribofuranosyl)-2(1H)-pyrimidinone

<400> SEQUENCE: 13
cgtcgttntt ggctc                                                    15

<210> SEQ ID NO 14
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 4-amino-3-hydro-7-(2-deoxy-beta-D-
      ribofuranosyl)-pyrrolo[2,3-d]pyrimidin-2-one

<400> SEQUENCE: 14
gagccaanaa cgacg                                                    15

<210> SEQ ID NO 15
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 4-amino-N1-methyl-5-(1'-beta-D-2'-
      deoxyribofuranosyl)-2(1H)-pyrimidinone

<400> SEQUENCE: 15
cgtcgtnnnt ggctc                                                    15

<210> SEQ ID NO 16
<211> LENGTH: 15
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 4-amino-3-hydro-7-(2-deoxy-beta-D-
      ribofuranosyl)-pyrrolo[2,3-d]pyrimidin-2-one

<400> SEQUENCE: 16
gagccannna cgacg                                                    15

<210> SEQ ID NO 17
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 4-amino-N1-methyl-5-(1'-beta-D-2'-
      deoxyribofuranosyl)-2(1H)-pyrimidinone
<220> FEATURE:
<221> NAME/KEY: misc_feature
<222> LOCATION: (8)..(8)
<223> OTHER INFORMATION: 4-amino-N1-methyl-5-(1'-beta-D-2'-
      deoxyribofuranosyl)-2(1H)-pyrimidinone
<220> FEATURE:
<221> NAME/KEY: misc_feature
<222> LOCATION: (10)..(10)
<223> OTHER INFORMATION: 4-amino-N1-methyl-5-(1'-beta-D-2'-
      deoxyribofuranosyl)-2(1H)-pyrimidinone

<400> SEQUENCE: 17
cgtcgntntn ggctc                                                    15

<210> SEQ ID NO 18
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 4-amino-3-hydro-7-(2-deoxy-beta-D-
      ribofuranosyl)-pyrrolo[2,3-d]pyrimidin-2-one
<220> FEATURE:
<221> NAME/KEY: misc_feature
<222> LOCATION: (8)..(8)
<223> OTHER INFORMATION: 4-amino-3-hydro-7-(2-deoxy-beta-D-
      ribofuranosyl)-pyrrolo[2,3-d]pyrimidin-2-one
<220> FEATURE:
<221> NAME/KEY: misc_feature
<222> LOCATION: (10)..(10)
<223> OTHER INFORMATION: 4-amino-3-hydro-7-(2-deoxy-beta-D-
      ribofuranosyl)-pyrrolo[2,3-d]pyrimidin-2-one

<400> SEQUENCE: 18
gagccnanan cgacg                                                    15

<210> SEQ ID NO 19
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 4-amino-N1-methyl-5-(1'-beta-D-2'-
      deoxyribofuranosyl)-2(1H)-pyrimidinone
```

<400> SEQUENCE: 19
cgtcgnnnnn ggctc                                                    15

<210> SEQ ID NO 20
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 4-amino-3-hydro-7-(2-deoxy-beta-D-
      ribofuranosyl)-pyrrolo[2,3-d]pyrimidin-2-one

<400> SEQUENCE: 20
gagccnnnnn cgacg                                                    15

<210> SEQ ID NO 21
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 2'-deoxy-7-deazaxanthosine

<400> SEQUENCE: 21
cgtcgttntt ggctc                                                    15

<210> SEQ ID NO 22
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 2,6-diamino-3-nitro-5-(1'-beta-D-2'-
      deoxyribofuranosyl)-pyridine

<400> SEQUENCE: 22
gagccaanaa cgacg                                                    15

<210> SEQ ID NO 23
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 2'-deoxy-7-deazaxanthosine

<400> SEQUENCE: 23
cgtcgtnnnt ggctc                                                    15

<210> SEQ ID NO 24
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature

```
<222> LOCATION: (7)..(9)
<223> OTHER INFORMATION: 2,6-diamino-3-nitro-5-(1'-beta-D-2'-
      deoxyribofuranosyl)-pyridine

<400> SEQUENCE: 24
gagccannna cgacg                                                    15

<210> SEQ ID NO 25
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2'-deoxy-7-deazaxanthosine
<220> FEATURE:
<221> NAME/KEY: misc_feature
<222> LOCATION: (8)..(8)
<223> OTHER INFORMATION: 2'-deoxy-7-deazaxanthosine
<220> FEATURE:
<221> NAME/KEY: misc_feature
<222> LOCATION: (10)..(10)
<223> OTHER INFORMATION: 2'-deoxy-7-deazaxanthosine

<400> SEQUENCE: 25
cgtcgntntn ggctc                                                    15

<210> SEQ ID NO 26
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2,6-diamino-3-nitro-5-(1'-beta-D-2'-
      deoxyribofuranosyl)-pyridin
<220> FEATURE:
<221> NAME/KEY: misc_feature
<222> LOCATION: (8)..(8)
<223> OTHER INFORMATION: 2,6-diamino-3-nitro-5-(1'-beta-D-2'-
      deoxyribofuranosyl)-pyridin
<220> FEATURE:
<221> NAME/KEY: misc_feature
<222> LOCATION: (10)..(10)
<223> OTHER INFORMATION: 2,6-diamino-3-nitro-5-(1'-beta-D-2'-
      deoxyribofuranosyl)-pyridin

<400> SEQUENCE: 26
gagccnanan cgacg                                                    15

<210> SEQ ID NO 27
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 2'-deoxy-7-deazaxanthosine

<400> SEQUENCE: 27
cgtcgnnnnn ggctc                                                    15

<210> SEQ ID NO 28
<211> LENGTH: 15
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 2,6-diamino-3-nitro-5-(1'-beta-D-2'-
      deoxyribofuranosyl)-pyridine

<400> SEQUENCE: 28
gagccnnnnn cgacg                                                     15

<210> SEQ ID NO 29
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 8-(beta-D-2'-deoxyribofuranosyl)imidazo[1,2-a]-
      1,3,5-triazine-2(8H)-4(3H)-dione

<400> SEQUENCE: 29
cgtcgttntt ggctc                                                     15

<210> SEQ ID NO 30
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 2,4-diamino-5-(1'-beta-D-2'-
      deoxyribofuranosyl)-pyrimidine

<400> SEQUENCE: 30
gagccaanaa cgacg                                                     15

<210> SEQ ID NO 31
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 2'-deoxyxanthosine

<400> SEQUENCE: 31
cgtcgttntt ggctc                                                     15

<210> SEQ ID NO 32
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 8-(beta-D-2'-deoxyribofuranosyl)imidazo[1,2-a]-
      1,3,5-triazine-2(8H)-4(3H)-dione

<400> SEQUENCE: 32
cgtcgtnnnt ggctc                                                     15
```

```
<210> SEQ ID NO 33
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 2,4-diamino-5-(1'-beta-D-2'-
      deoxyribofuranosyl)-pyrimidine

<400> SEQUENCE: 33
gagccannna cgacg                                                    15

<210> SEQ ID NO 34
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 2'-deoxyxanthosine

<400> SEQUENCE: 34
cgtcgtnnnt ggctc                                                    15

<210> SEQ ID NO 35
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 8-(beta-D-2'-deoxyribofuranosyl)imidazo[1,2-a]-
      1,3,5-triazine-2(8H)-4(3H)-dione
<220> FEATURE:
<221> NAME/KEY: misc_feature
<222> LOCATION: (8)..(8)
<223> OTHER INFORMATION: 8-(beta-D-2'-deoxyribofuranosyl)imidazo[1,2-a]-
      1,3,5-triazine-2(8H)-4(3H)-dione
<220> FEATURE:
<221> NAME/KEY: misc_feature
<222> LOCATION: (10)..(10)
<223> OTHER INFORMATION: 8-(beta-D-2'-deoxyribofuranosyl)imidazo[1,2-a]-
      1,3,5-triazine-2(8H)-4(3H)-dione

<400> SEQUENCE: 35
cgtcgntntn ggctc                                                    15

<210> SEQ ID NO 36
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2,4-diamino-5-(1'-beta-D-2'-
      deoxyribofuranosyl)-pyrimidine
<220> FEATURE:
<221> NAME/KEY: misc_feature
<222> LOCATION: (8)..(8)
<223> OTHER INFORMATION: 2,4-diamino-5-(1'-beta-D-2'-
      deoxyribofuranosyl)-pyrimidine
<220> FEATURE:
```

-continued

```
<221> NAME/KEY: misc_feature
<222> LOCATION: (10)..(10)
<223> OTHER INFORMATION: 2,4-diamino-5-(1'-beta-D-2'-
      deoxyribofuranosyl)-pyrimidine

<400> SEQUENCE: 36
gagccnanan cgacg                                                      15

<210> SEQ ID NO 37
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2'-deoxyxanthosine
<220> FEATURE:
<221> NAME/KEY: misc_feature
<222> LOCATION: (8)..(8)
<223> OTHER INFORMATION: 2'-deoxyxanthosine
<220> FEATURE:
<221> NAME/KEY: misc_feature
<222> LOCATION: (10)..(10)
<223> OTHER INFORMATION: 2'-deoxyxanthosine

<400> SEQUENCE: 37
cgtcgntntn ggctc                                                      15

<210> SEQ ID NO 38
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 8-(beta-D-2'-deoxyribofuranosyl)imidazo[1,2-a]-
      1,3,5-triazine-2(8H)-4(3H)-dione

<400> SEQUENCE: 38
cgtcgnnnnn ggctc                                                      15

<210> SEQ ID NO 39
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 2,4-diamino-5-(1'-beta-D-2'-
      deoxyribofuranosyl)-pyrimidine

<400> SEQUENCE: 39
gagccnnnnn cgacg                                                      15

<210> SEQ ID NO 40
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 2'-deoxyxanthosine
```

-continued

```
<400> SEQUENCE: 40
cgtcgnnnnn ggctc                                                    15

<210> SEQ ID NO 41
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (7)..(7)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (8)..(8)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (9)..(9)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (10)..(10)
<223> OTHER INFORMATION: 6-amino-3-(2'-deoxy-D-ribofuranosyl)-5-nitro-
      1H-pyridin-2-one

<400> SEQUENCE: 41
gagccnnnnn cgacg                                                    15

<210> SEQ ID NO 42
<211> LENGTH: 15
<212> TYPE: DNA
<213> ORGANISM: Artificial Sequence
<220> FEATURE:
<223> OTHER INFORMATION: Synthetic

<400> SEQUENCE: 42 gagcctttttt cgacg                                                   15

<210> SEQ ID NO 43
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (2)..(3)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (5)..(5)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (6)..(6)
<223> OTHER INFORMATION: 4-amino-N1-methyl-5-(1'-beta-D-2'-
```

```
        deoxyribofuranosyl)-2(1H)-pyrimidinone
<220> FEATURE:
<221> NAME/KEY: misc_feature
<222> LOCATION: (7)..(7)
<223> OTHER INFORMATION: 2,6-diamino-3-nitro-5-(1'-beta-D-2'-
        deoxyribofuranosyl)-pyridine
<220> FEATURE:
<221> NAME/KEY: misc_feature
<222> LOCATION: (10)..(11)
<223> OTHER INFORMATION: 2,6-diamino-3-nitro-5-(1'-beta-D-2'-
        deoxyribofuranosyl)-pyridine
<220> FEATURE:
<221> NAME/KEY: misc_feature
<222> LOCATION: (12)..(12)
<223> OTHER INFORMATION: 4-amino-N1-methyl-5-(1'-beta-D-2'-
        deoxyribofuranosyl)-2(1H)-pyrimidinone
<220> FEATURE:
<221> NAME/KEY: misc_feature
<222> LOCATION: (14)..(14)
<223> OTHER INFORMATION: 4-amino-N1-methyl-5-(1'-beta-D-2'-
        deoxyribofuranosyl)-2(1H)-pyrimidinone

<400> SEQUENCE: 43
nnntnnnttn nntnt                                                15

<210> SEQ ID NO 44
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy-2-aminoadenosine
<220> FEATURE:
<221> NAME/KEY: misc_feature
<222> LOCATION: (2)..(2)
<223> OTHER INFORMATION: 4-amino-3-hydro-7-(2-deoxy-beta-D-
        ribofuranosyl)-pyrrolo[2,3-d]pyrimidin-2-one
<220> FEATURE:
<221> NAME/KEY: misc_feature
<222> LOCATION: (3)..(3)
<223> OTHER INFORMATION: 2'-deoxy-2-aminoadenosine
<220> FEATURE:
<221> NAME/KEY: misc_feature
<222> LOCATION: (4)..(4)
<223> OTHER INFORMATION: 4-amino-3-hydro-7-(2-deoxy-beta-D-
        ribofuranosyl)-pyrrolo[2,3-d]pyrimidin-2-one
<220> FEATURE:
<221> NAME/KEY: misc_feature
<222> LOCATION: (5)..(6)
<223> OTHER INFORMATION: 2'-deoxy-7-deazaxanthosine
<220> FEATURE:
<221> NAME/KEY: misc_feature
<222> LOCATION: (7)..(8)
<223> OTHER INFORMATION: 2'-deoxy-2-aminoadenosine
<220> FEATURE:
<221> NAME/KEY: misc_feature
<222> LOCATION: (9)..(9)
<223> OTHER INFORMATION: 2'-deoxy-7-deazaxanthosine
<220> FEATURE:
<221> NAME/KEY: misc_feature
<222> LOCATION: (10)..(10)
<223> OTHER INFORMATION: 4-amino-3-hydro-7-(2-deoxy-beta-D-
        ribofuranosyl)-pyrrolo[2,3-d]pyrimidin-2-one
<220> FEATURE:
<221> NAME/KEY: misc_feature
<222> LOCATION: (11)..(11)
<223> OTHER INFORMATION: 7-amino-9-(1'-beta-D-2'-deoxyribofuranosyl)-
        imidazo[1,2-c]pyrimidin-5(1H)-one
<220> FEATURE:
<221> NAME/KEY: misc_feature
<222> LOCATION: (12)..(12)
<223> OTHER INFORMATION: 2'-deoxy-2-aminoadenosine
<220> FEATURE:
<221> NAME/KEY: misc_feature
```

<222> LOCATION: (13)..(14)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (15)..(15)
<223> OTHER INFORMATION: 2'-deoxy-7-deazaxanthosine

<400> SEQUENCE: 44
nnnnnnnnnn nnnnn                                                       15

<210> SEQ ID NO 45
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy-2-aminoadenosine
<220> FEATURE:
<221> NAME/KEY: misc_feature
<222> LOCATION: (2)..(3)
<223> OTHER INFORMATION: 4-amino-3-hydro-7-(2-deoxy-beta-D-
      ribofuranosyl)-pyrrolo[2,3-d]pyrimidin-2-one
<220> FEATURE:
<221> NAME/KEY: misc_feature
<222> LOCATION: (4)..(4)
<223> OTHER INFORMATION: 2'-deoxy-7-deazaxanthosine
<220> FEATURE:
<221> NAME/KEY: misc_feature
<222> LOCATION: (5)..(5)
<223> OTHER INFORMATION: 4-amino-3-hydro-7-(2-deoxy-beta-D-
      ribofuranosyl)-pyrrolo[2,3-d]pyrimidin-2-one
<220> FEATURE:
<221> NAME/KEY: misc_feature
<222> LOCATION: (6)..(6)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (7)..(7)
<223> OTHER INFORMATION: 2'-deoxy-2-aminoadenosine
<220> FEATURE:
<221> NAME/KEY: misc_feature
<222> LOCATION: (8)..(9)
<223> OTHER INFORMATION: 2'-deoxy-7-deazaxanthosine
<220> FEATURE:
<221> NAME/KEY: misc_feature
<222> LOCATION: (10)..(11)
<223> OTHER INFORMATION: 2'-deoxy-2-aminoadenosine
<220> FEATURE:
<221> NAME/KEY: misc_feature
<222> LOCATION: (12)..(12)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (13)..(13)
<223> OTHER INFORMATION: 2'-deoxy-7-deazaxanthosine
<220> FEATURE:
<221> NAME/KEY: misc_feature
<222> LOCATION: (14)..(14)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (15)..(15)
<223> OTHER INFORMATION: 2'-deoxy-7-deazaxanthosine

<400> SEQUENCE: 45
nnnnnnnnnn nnnnn                                                       15

<210> SEQ ID NO 46

```
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (2)..(2)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (3)..(3)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (4)..(4)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (7)..(8)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (10)..(10)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (11)..(11)
<223> OTHER INFORMATION: 4-amino-N1-methyl-5-(1'-beta-D-2'-
      deoxyribofuranosyl)-2(1H)-pyrimidinone
<220> FEATURE:
<221> NAME/KEY: misc_feature
<222> LOCATION: (12)..(12)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (13)..(14)
<223> OTHER INFORMATION: 4-amino-N1-methyl-5-(1'-beta-D-2'-
      deoxyribofuranosyl)-2(1H)-pyrimidinone

<400> SEQUENCE: 46
nnnnttnntn nnnnt                                                15

<210> SEQ ID NO 47
<211> LENGTH: 15
<212> TYPE: DNA
<213> ORGANISM: Artificial Sequence
<220> FEATURE:
<223> OTHER INFORMATION: Synthetic

<400> SEQUENCE: 47
agagaaaaag gagga                                                15

<210> SEQ ID NO 48
<211> LENGTH: 15
<212> TYPE: DNA
<213> ORGANISM: Artificial Sequence
<220> FEATURE:
<223> OTHER INFORMATION: Synthetic

<400> SEQUENCE: 48
tcctcctttt tctct                                                15
```

-continued

<210> SEQ ID NO 49
<211> LENGTH: 15
<212> TYPE: DNA
<213> ORGANISM: Artificial Sequence
<220> FEATURE:
<223> OTHER INFORMATION: Synthetic

<400> SEQUENCE: 49
aggaggaaaa agaga                                                    15

<210> SEQ ID NO 50
<211> LENGTH: 15
<212> TYPE: DNA
<213> ORGANISM: Artificial Sequence
<220> FEATURE:
<223> OTHER INFORMATION: Synthetic

<400> SEQUENCE: 50 tctcttttc ctcct                                                     15

<210> SEQ ID NO 51
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(7)
<223> OTHER INFORMATION: 2'-deoxy-2-aminoadenosine
<220> FEATURE:
<221> NAME/KEY: misc_feature
<222> LOCATION: (8)..(8)
<223> OTHER INFORMATION: 4-amino-3-hydro-7-(2-deoxy-beta-D-
      ribofuranosyl)-pyrrolo[2,3-d]pyrimidin-2-one
<220> FEATURE:
<221> NAME/KEY: misc_feature
<222> LOCATION: (9)..(9)
<223> OTHER INFORMATION: 2'-deoxy-2-aminoadenosine
<220> FEATURE:
<221> NAME/KEY: misc_feature
<222> LOCATION: (10)..(10)
<223> OTHER INFORMATION: 4-amino-3-hydro-7-(2-deoxy-beta-D-
      ribofuranosyl)-pyrrolo[2,3-d]pyrimidin-2-one
<220> FEATURE:
<221> NAME/KEY: misc_feature
<222> LOCATION: (11)..(12)
<223> OTHER INFORMATION: 2'-deoxyxanthosine
<220> FEATURE:
<221> NAME/KEY: misc_feature
<222> LOCATION: (13)..(14)
<223> OTHER INFORMATION: 2'-deoxy-2-aminoadenosine
<220> FEATURE:
<221> NAME/KEY: misc_feature
<222> LOCATION: (15)..(15)
<223> OTHER INFORMATION: 2'-deoxyxanthosine
<220> FEATURE:
<221> NAME/KEY: misc_feature
<222> LOCATION: (16)..(16)
<223> OTHER INFORMATION: 4-amino-3-hydro-7-(2-deoxy-beta-D-
      ribofuranosyl)-pyrrolo[2,3-d]pyrimidin-2-one
<220> FEATURE:
<221> NAME/KEY: misc_feature
<222> LOCATION: (17)..(17)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (18)..(18)
<223> OTHER INFORMATION: 2'-deoxy-2-aminoadenosine
<220> FEATURE:
<221> NAME/KEY: misc_feature
<222> LOCATION: (19)..(20)
<223> OTHER INFORMATION: 7-amino-9-(1'-beta-D-2'-deoxyribofuranosyl)-

```
      imidazo[1,2-c]pyrimidin-5(1H)-one
<220> FEATURE:
<221> NAME/KEY: misc_feature
<222> LOCATION: (21)..(21)
<223> OTHER INFORMATION: 2'-deoxyxanthosine

<400> SEQUENCE: 51
nnnnnnnnnn nnnnnnnnnn n                                                   21

<210> SEQ ID NO 52
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: 2,4-diamino-5-(1'-beta-D-2'-
      deoxyribofuranosyl)-pyrimidine
<220> FEATURE:
<221> NAME/KEY: misc_feature
<222> LOCATION: (8)..(8)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (9)..(9)
<223> OTHER INFORMATION: 2,4-diamino-5-(1'-beta-D-2'-
      deoxyribofuranosyl)-pyrimidine
<220> FEATURE:
<221> NAME/KEY: misc_feature
<222> LOCATION: (10)..(10)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (13)..(14)
<223> OTHER INFORMATION: 2,4-diamino-5-(1'-beta-D-2'-
      deoxyribofuranosyl)-pyrimidine
<220> FEATURE:
<221> NAME/KEY: misc_feature
<222> LOCATION: (16)..(16)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (17)..(17)
<223> OTHER INFORMATION: 4-amino-N1-methyl-5-(1'-beta-D-2'-
      deoxyribofuranosyl)-2(1H)-pyrimidinone
<220> FEATURE:
<221> NAME/KEY: misc_feature
<222> LOCATION: (18)..(18)
<223> OTHER INFORMATION: 2,4-diamino-5-(1'-beta-D-2'-
      deoxyribofuranosyl)-pyrimidine
<220> FEATURE:
<221> NAME/KEY: misc_feature
<222> LOCATION: (19)..(20)
<223> OTHER INFORMATION: 4-amino-N1-methyl-5-(1'-beta-D-2'-
      deoxyribofuranosyl)-2(1H)-pyrimidinone

<400> SEQUENCE: 52 tttttttnnnn ttnntnnnnn t                                                  21

<210> SEQ ID NO 53
<211> LENGTH: 21
<212> TYPE: DNA
<213> ORGANISM: Artificial Sequence
<220> FEATURE:
<223> OTHER INFORMATION: synthetic

<400> SEQUENCE: 53
aaaaaaagag aaaaaggagg a                                                   21
```

```
<210> SEQ ID NO 54
<211> LENGTH: 21
<212> TYPE: DNA
<213> ORGANISM: Artificial Sequence
<220> FEATURE:
<223> OTHER INFORMATION: synthetic

<400> SEQUENCE: 54
tttttttctc tttttcctcc t                                        21

<210> SEQ ID NO 55
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(8)
<223> OTHER INFORMATION: 2,4-diamino-5-(1'-beta-D-2'-
      deoxyribofuranosyl)-pyrimidine

<400> SEQUENCE: 55
cttatanntt tataag                                              16
```

MOLECULAR RECOGNITION SYSTEMS WITH PYRIMIDINE ANALOG PAIRING

CROSS REFERENCE TO RELATED APPLICATION

This application is a continuation-in-part of currently pending U.S. patent application Ser. No. 16/111,590, entitled "Molecular Recognition Systems with Pyrimidine Analog Pairing", which was filed 24 Aug. 2018, which is a continuation-in-part of U.S. patent application Ser. No. 15/461,073, now issued as U.S. patent Ser. No. 10/059,737, which was filed 16 Mar. 2017, and also entitled "Molecular Recognition Systems with Pyrimidine Analog Pairing".

STATEMENT OF RIGHTS TO INVENTIONS MADE UNDER FEDERALLY SPONSORED RESEARCH

This invention was made with government support under NNX14AK37G, awarded by the National Aeronautics and Space Administration. The government has certain rights in the invention.

THE NAMES OF THE PARTIES TO A JOINT RESEARCH AGREEMENT

Not applicable

INCORPORATION-BY-REFERENCE OF MATERIAL SUBMITTED ON A COMPACT DISC

None

BACKGROUND OF THE INVENTION

(1) Field of the Invention

The field of this invention is molecular recognition, which comprises a process by which one molecule interacts with a specific second molecule, or by which a portion of a single molecule interacts with another specific portion of the same molecule. This invention relates to molecular recognition that follows simple rules. Further, the molecular recognition is between molecules that are analogs of DNA and RNA, meaning that they are built from a small set of molecular building blocks that are linked together by phosphate diester groups, and where the molecular building blocks comprise a sugar (ribose, 2'-deoxyribose, or an analog) attached to a heterocycle. The molecular recognition rules that they follow differ, however, from the rules followed by DNA and RNA, in that the rules governing the molecular recognition of the instant invention break the rules of size complementarity followed in molecular recognition between and within strands of DNA and RNA.

(2) Description of Related Art

Molecular technology frequently requires that molecules bind specifically to other molecules, and molecules that adopt a fold. Only rarely, however, does molecular recognition and/or folding follow simple rules. The archetypal example of rule-based molecular recognition and folding is displayed by nucleic acids, DNA and RNA. Here, an oligonucleotide or oligonucleotide analog, either in full length or in part, binds in an anti-parallel orientation to a complementary oligonucleotide (or part) according to Watson and Crick rules of nucleobase pairing. Those rules pair adenine (A) (or 2-aminoadenine) with thymine (T) (or uracil, U), and pair guanine (G) with cytosine (C), with complementary strands anti-parallel to one another. The same rules describe the molecular interaction observed when a segment of a single oligonucleotide molecule interacts with another segment of the same oligonucleotide, for example, to form a hairpin.

These Watson-Crick pairing rules are understood in the art to be the consequence of two molecular principles of complementarity. The first is size complementarity. Here, molecular recognition is taught to require that a large purine nucleobase on one of the two interacting oligonucleotides pair with a small pyrimidine nucleobase on the other.

The second rule is hydrogen bonding complementarity, where hydrogen bonding donors on one of the two interacting moieties match with hydrogen bonding acceptors on the other. In DNA and RNA, hydrogen bond donors are heteroatoms (nitrogen or oxygen) bearing a hydrogen, while hydrogen bond acceptors are heteroatoms (nitrogen or oxygen) with unshared electrons.

In natural DNA and RNA, these rules of molecular recognition are implemented using standard pyrimidines, thymine (or uracil) and cytosine, all having a six membered ring, and standard purines (adenine and guanine), a ring system composed of a fused five-six ring system. In both cases, a middle hydrogen bonding moiety allows the two ring systems to interact. Additional functional groups appended to each of the ring systems provide hydrogen bonding moieties on either side of the central hydrogen bond. The A:T nucleobase pair uses this hydrogen bonding pattern only partly; it is completely used in the 2-aminoA:T base pair.

The art teaches that size complementarity is more important than hydrogen bonding complementarity [Goodman, M. F. (1999) On the wagon. DNA polymerase joins "H-bonds anonymous". *Nature Biotech.* 17, 640-641.]. Indeed, this teaching continues even today [Malyshev et al. (2014) A semi-synthetic organism with an expanded genetic alphabet. Nature 509.7500: 385-388] [Zhang et al. (2017) A semisynthetic organism engineered for the stable expansion of the genetic alphabet. *Proc. Natl. Acad. Sci. USA:* 201616443]. Here, an additional pair is taught that lacks inter-strand hydrogen bonding of any kind, but purportedly still fits the rules of size complementarity.

Figure 9:
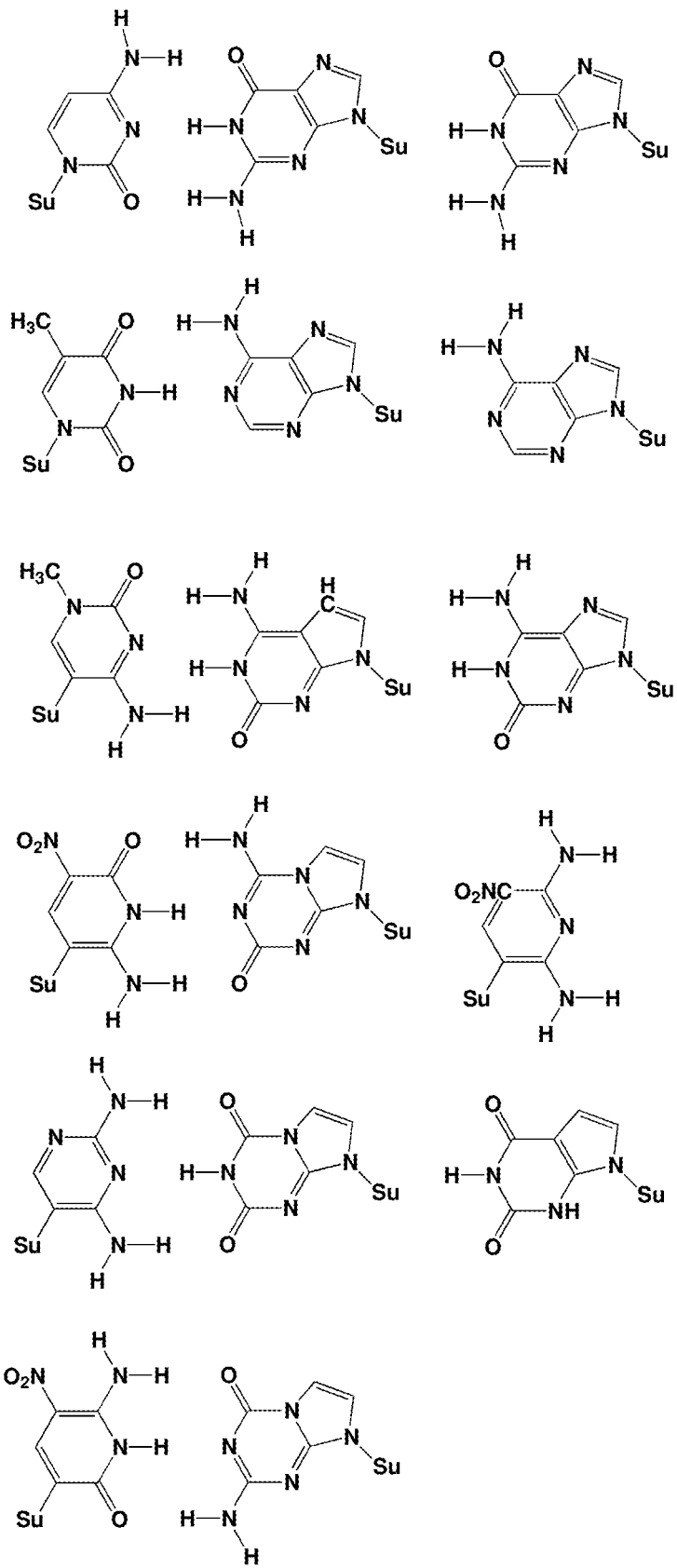

These rules have been generalized to include nucleobases where hydrogen bonding units are swapped. This creates new nucleobase pairs joined by nonstandard patterns of hydrogen bonding. For example, U.S. Pat. No. 5,432,272 disclosed eight additional nucleobases that form four additional pairs by changing the pattern of hydrogen bond donor and acceptor groups presented by a nucleobase to the nucleobase on a complementary oligonucleotide analog. These disclosures showed that the geometry of the Watson-Crick nucleobase pair could accommodate as many as 12 nucleobases forming 6 mutually exclusive pairs (FIG. 9).

From time to time, reports have appeared in the literature where the Watson-Crick size complementarity has been violated. For example, in 2003, Geyer et al. determine the melting temperatures of a large number of duplexes containing standard and nonstandard pairs [Geyer, C. R., Battersby, T. R., Benner, S. A. (2003) Nucleobase pairing in expanded Watson-Crick like genetic information systems. The nucleobases. *Structure* 11, 1485-1498]. The overwhelming number of these duplexes were formed with pairs that obey the size complementarity rule. However, contained within the ca. 100 duplexes reported were individual cases where a small pyrimidine analog was paired with another small pyrimidine analog, while retaining hydrogen bonding complementarity. Duplexes violating Watson-Crick geometry in this way (small pairing with small) had lower stability, and the investigation was not continued to examine two or more of these "skinny" pairs in a single duplex.

Geyer et al. [op. cit.] also disclosed duplexes where a single large purine analogue was paired with another large purine. Again, the stability of the duplex was generally lower than the stability of duplexes containing fully size complementary pairs, and the investigation was not continued to examine two or more of these "fat" pairs in a single duplex. Further, the pairing was proposed to arise in a geometry where one large purine (or purine analog) case had rotated around the glycosidic bond to present its "Hoogsteen" edge to its pairing partner. This restored, in large part, imperfect size complementarity between the two purines, Fat pairs without this rotation are, however, proposed elsewhere in the art. For example, Seela et al. proposed a "fat" pair between isoguanosine and a functionalized imidazo[1,2-a]-1,3,5-triazine (FIG. 1) [Seela, F., Amberg, S., Melenewski, A., Rosemeyer, H. (2001) 5-Aza-7-deazaguanine DNA: Recognition and strand orientation of oligonucleotides incorporating anomeric imidazo[1,2-a]-1,3,5-triazine nucleosides. Helv. Chim. Acta 84, 1996-2014]. This was an example where the Watson-Crick size complementarity rule is violated, assuming that no rotation occurred. In their model, they assumed that three hydrogen bonds were formed between the purine and the purine analog. Further, they reported molecular recognition between two oligonucleotide strands involving one, two consecutive, or three consecutive pairs.

Figure 2:
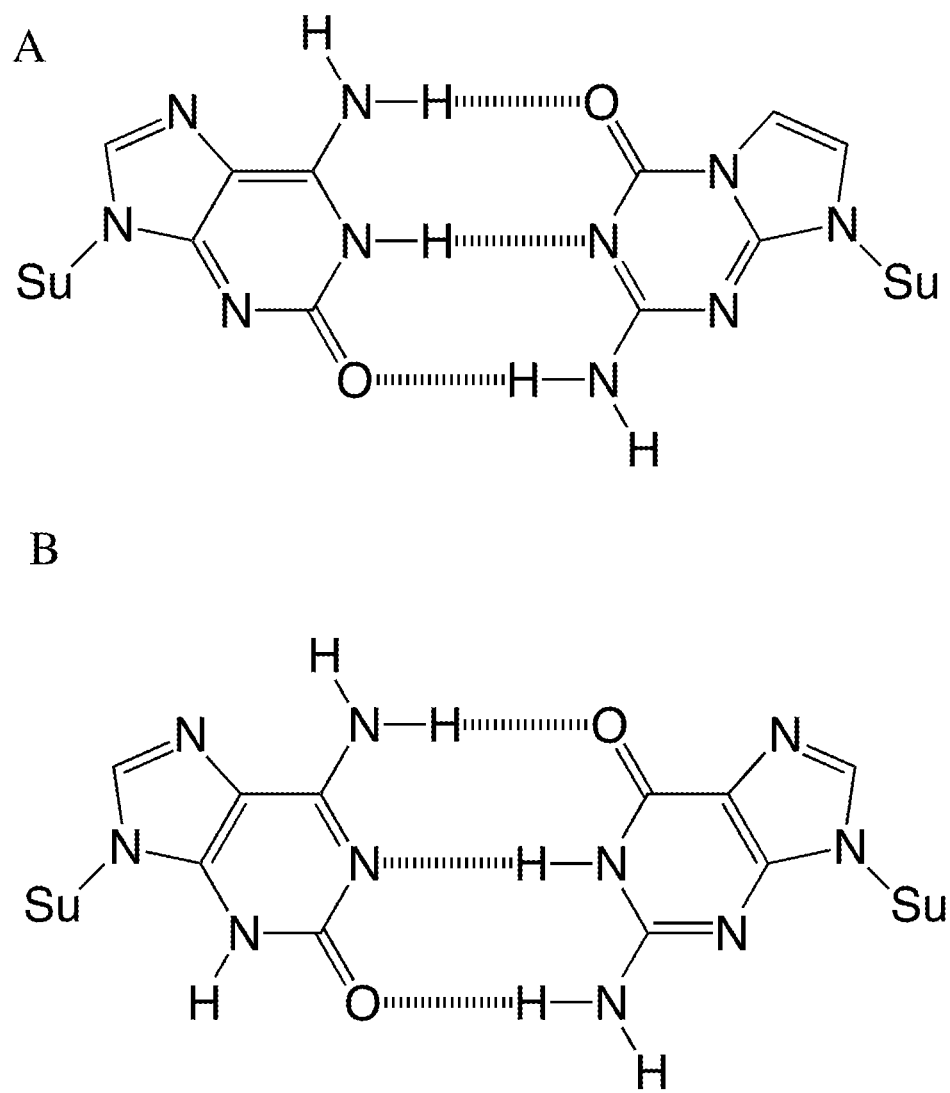

Heuberger and Switzer also reported interaction between the same purine isoguanosine, but pairs to another standard purine, guanine (FIG. 2) [Heuberger, B. D., Switzer, C. (2008). An alternative nucleobase code: Characterization of purine-purine DNA double helices bearing guanine-isoguanine and diaminopurine 7-deaza-xanthine base pairs. *Chem Bio Chem*, 9, 2779-2783]. Here, however, a tautomer of isoguanine was proposed, the N3(H) tautomer (FIG. 2). This tautomer of isoguanine is different from the one proposed by Seela in its interaction with the triazine. This suggested that this pairing that violates size commentary rules may not be specific only in the second tautomer was hydrogen bonding complementarity possible.

Isoguanine was also examined as a partner with guanine to give another "fat" pair by Buckley et al. and Kuruvilla et al. [Buckley, R., Enekwa, C. D., Williams L. D., Hud, N. V. (2011) Molecular recognition of Watson-Crick-like purine-purine base pairs. *Chem Bio Chem*, 12, 2155-2158] [Kuruvilla, E., Schuster, G. B., Hud, N. V. (2013) Enhanced nonenzymatic ligation of homopurine miniduplexes: Support for greater base stacking in a Pre-RNA World. *Chem Bio Chem*, 14, 45-48]. No biophysical data were presented in these publications. Nevertheless, the art presumes an N3(H) tautomer for isoguanine, because this is the tautomer that can form three inter-pair hydrogen bonds with a guanine partner in a fat, anti-anti, pair.

A few items of art also examine the purine:purine analog pair between diaminopurine and 7-deazaxanthine [Heuberger, B. D. and Switzer, C. (2008) An alternative nucleobase code: Characterization of purine-purine DNA double helices bearing guanine-isoguanine and diaminopurine 7-deaza-xanthine base pairs. *Chem Bio Chem* 9, 2779-2783] [Kuruvilla, E., Schuster, G. B., Hud, N. V. (2013) Enhanced nonenzymatic ligation of homopurine miniduplexes. Support for greater base stacking in a pre-RNA World. *Chem Bio Chem* 14, 45-48.]. The first paper suggested the possibility of an "alternative code", meaning a rule-based molecular recognition system, where isoguanosine (as its N3(H) tautomer) pairs with guanine, and diaminopurine pairs with xanthosine or 7-deazaxanthosine. Here, the longest duplex examined had 12 of these "fat" pairs, with a melting temperature higher (60.3 versus 55.3° C. than a reference pair that obeyed the size complementarity rule.

Finally, a purine:purine pair was examined by Buckley et al., where the "fat" pair was joined by only two hydrogen bonds [Buckley, R., Enekwa, C. D., Williams L. D. and Hud, N. V. (2011) Molecular recognition of Watson-Crick-like purine-purine base pairs. *Chem Bio Chem*, 12, 2155-2158]. No biophysical data were presented unique to this paper. Nevertheless, the stability of "fat" pairs was attributed to greater stacking energy, possible with the two larger ring systems.

BRIEF SUMMARY OF THE INVENTION

This invention is based on the discovery of an unexpected stability of duplexes that violate the Watson-Crick size complementary pairing rule, but where that violation does involve the pairing of large purines with other purines. Instead, that rule is violated by pairing a small heterocycle with another small heterocycle to give a "skinny" pair. Thus, this invention comprises compositions of matter that are one or more oligonucleotides or oligonucleotide analogs that form extended duplex regions where pyrimidine analogs pair with other pyrimidine analogs, at least three consecutively. This pairing does not benefit by greater stacking interactions. However, each pair is joined by three hydrogen bonds, and the chains forming the duplexes have an antiparallel orientation. When the invention concern a single oligonucleotide or oligonucleotide analog, this skinny pairing enables a folded form, again where the fold is joined by antiparallel strands that can form multiple consecutive skinny pairs.

BRIEF DESCRIPTION OF THE SEVERAL VIEWS OF THE DRAWING(S)

FIG. 1. Isolated cases from the art of "fat" pairs between two purine analogs, including one that donor:acceptor:donor pattern, and the other presenting the hydrogen bonding acceptor:donor:acceptor pattern. Su=sugar of oligonucleotide, the point of attachment of the heterocycle to the oligonucleotide chain.

A. From Shaikh, K. I., Leonard, P. and Seela, F. (2007) 7-Deaza-2'-deoxyxanthosine: nucleobase protection and base pairing of oligonucleotides. *Nucleosides, Nucleotides, and Nucleic Acids*, 26, 737-741.

B. From Kuruvilla, E., Schuster, G. B. and Hud, N. V. (2013) Enhanced nonenzymatic ligation of homopurine miniduplexes: Support for greater base stacking in a pre-RNA world. *Chem Bio Chem*, 14, 45-48.

C. From: Heuberger, B. D. and Switzer, C. (2008) An alternative nucleobase code: characterization of purine-purine DNA double helices bearing guanine-isoguanine and diaminopurine 7-deaza-xanthine base Pairs. *Chem Bio Chem*, 9, 2779-2783.

D. From: Buckley, R., Enekwa, C. D., Williams L. D. and Hud, N. V. (2011) Molecular recognition of Watson-Crick-like purine-purine base pairs. *Chem Bio Chem*, 12, 2155-2158.

FIG. 2. Isolated cases from the art of "fat" pairs between two purine analogs, one that is isoguanine, the other that matches respectively the N1(H) tautomer of isoguanosine, the other that matches the N3(H) tautomer of isoguanosine. Su=sugar of oligonucleotide, the point of attachment of the heterocycle to the oligonucleotide chain.

A. From Seela, F., Amberg, S., Melenewski, A. and Rosemeyer, H. (2001) 5-Aza-7-deazaguanine DNA: Recognition and strand orientation of oligonucleotides incorporating anomeric imidazo[1,2-a]-1,3,5-triazine nucleosides. *Helv. Chim. Acta,* 84, 1996-2014.

B. From: Heuberger, B. D. and Switzer, C. (2008) An Alternative Nucleobase Code: Characterization of Purine-Purine DNA Double Helices Bearing Guanine-Isoguanine and Diaminopurine 7-Deaza-Xanthine Base Pairs. *Chem Bio Chem,* 9, 2779-2783. Kuruvilla, E., Schuster, G. B. and Hud, N. V. (2013) Enhanced nonenzymatic ligation of homopurine miniduplexes: Support for greater base stacking in a pre-RNA World. *Chem Bio Chem,* 14, 45-48. Buckley, R., Enekwa, C. D., Williams L. D. and Hud, N. V. (2011) Molecular recognition of Watson-Crick-like purine-purine base pairs. *Chem Bio Chem,* 12, 2155-2158.

Figure 3:
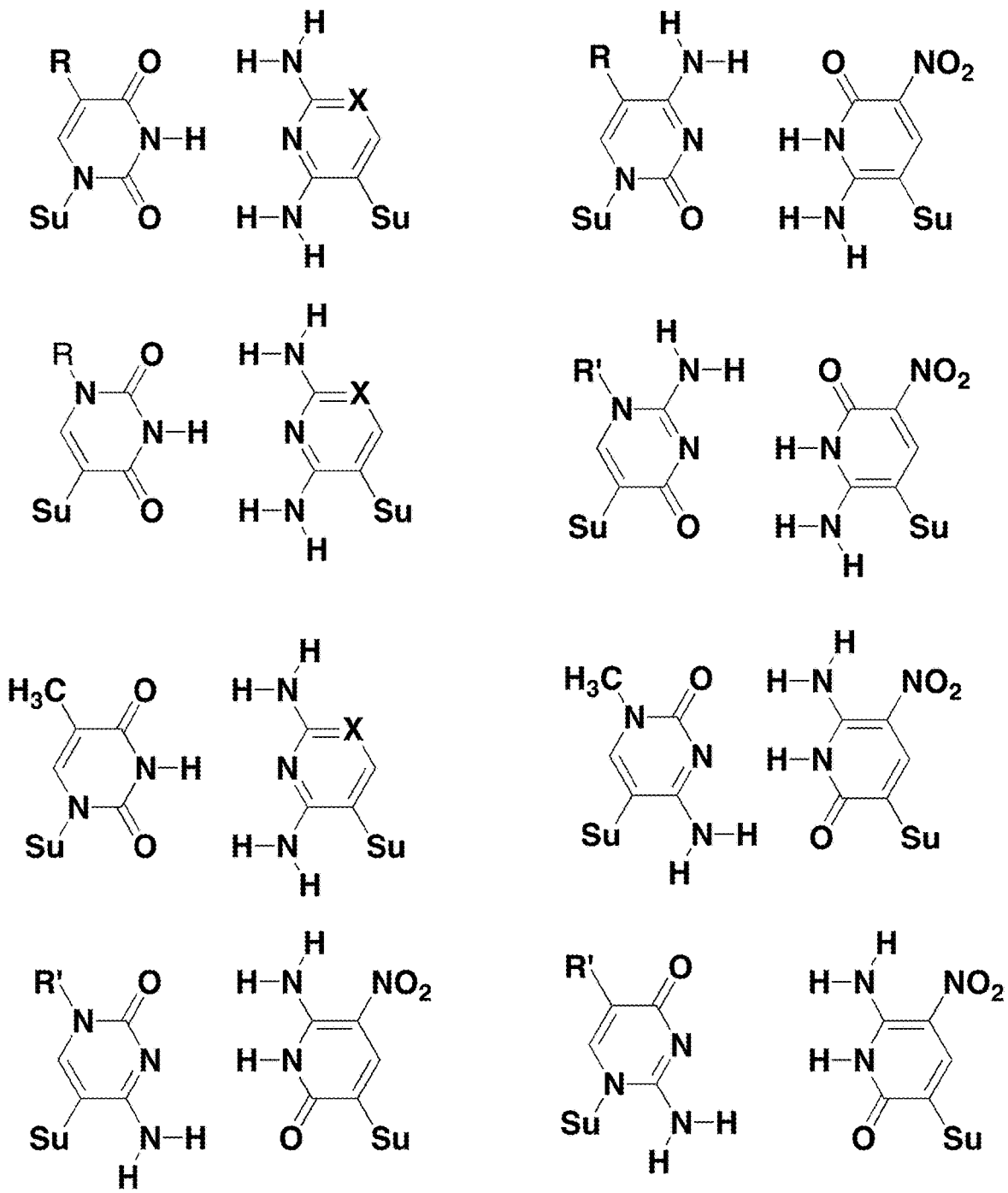

FIG. 3. Skinny pairs of the instant invention. Note that more than one heterocycle can implement the various hydrogen bonding patterns. R'=CH$_3$, alkyl, alkenyl, alkynyl functionalized alkyl, alkenyl, or alkynyl. Su=sugar of oligonucleotide, the point of attachment of the heterocycle to the oligonucleotide chain. R=H, CH$_3$, alkyl, alkenyl, alkynyl functionalized alkyl, alkenyl, or alkynyl. X=N, C—NO$_2$.

Figure 4:
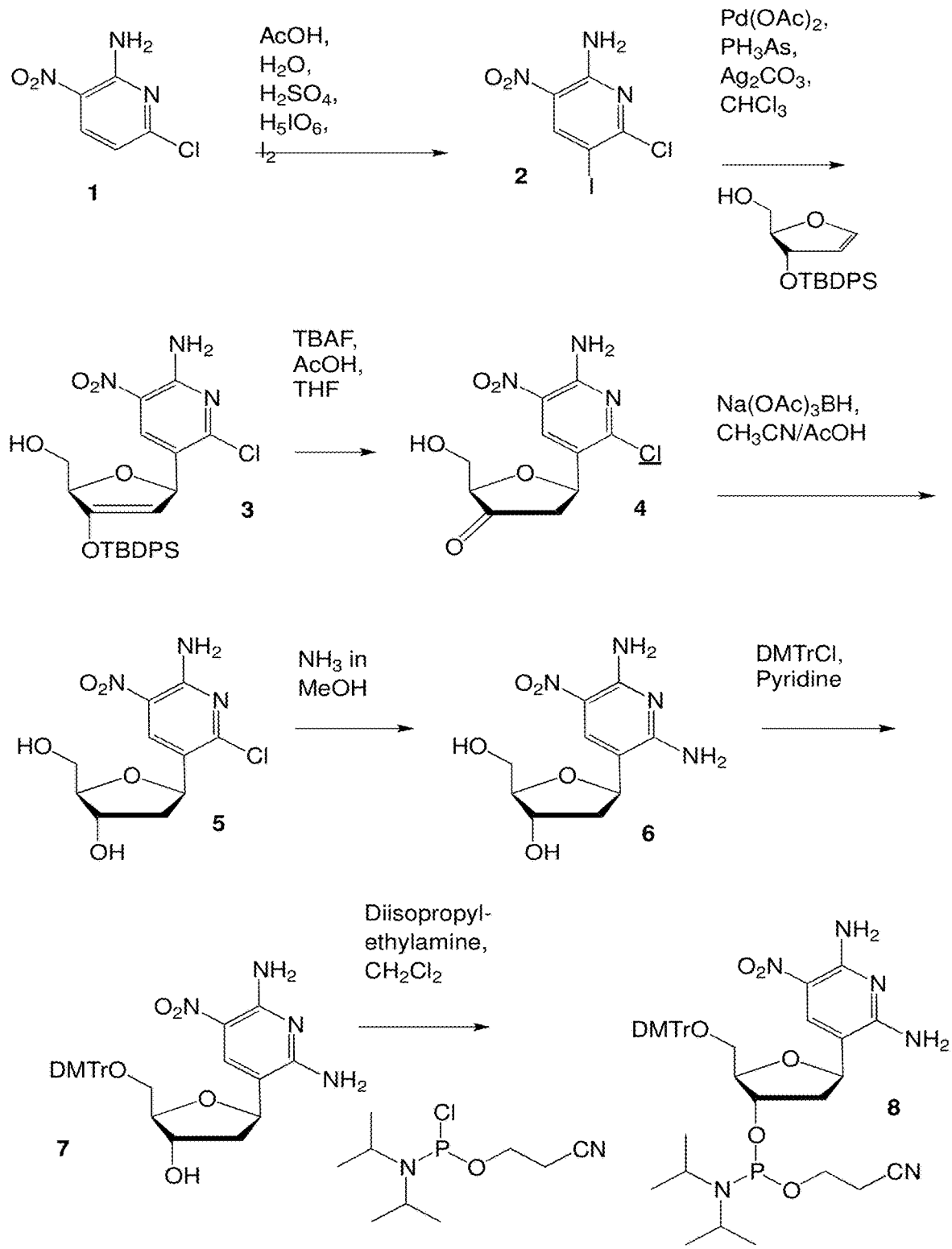

FIG. 4. Synthetic route to make the protected phosphoramidite carrying the small 2,6-diamino-3-nitropyridine, which implements the donor-acceptor-donor K hydrogen bonding pattern.

Figure 5:
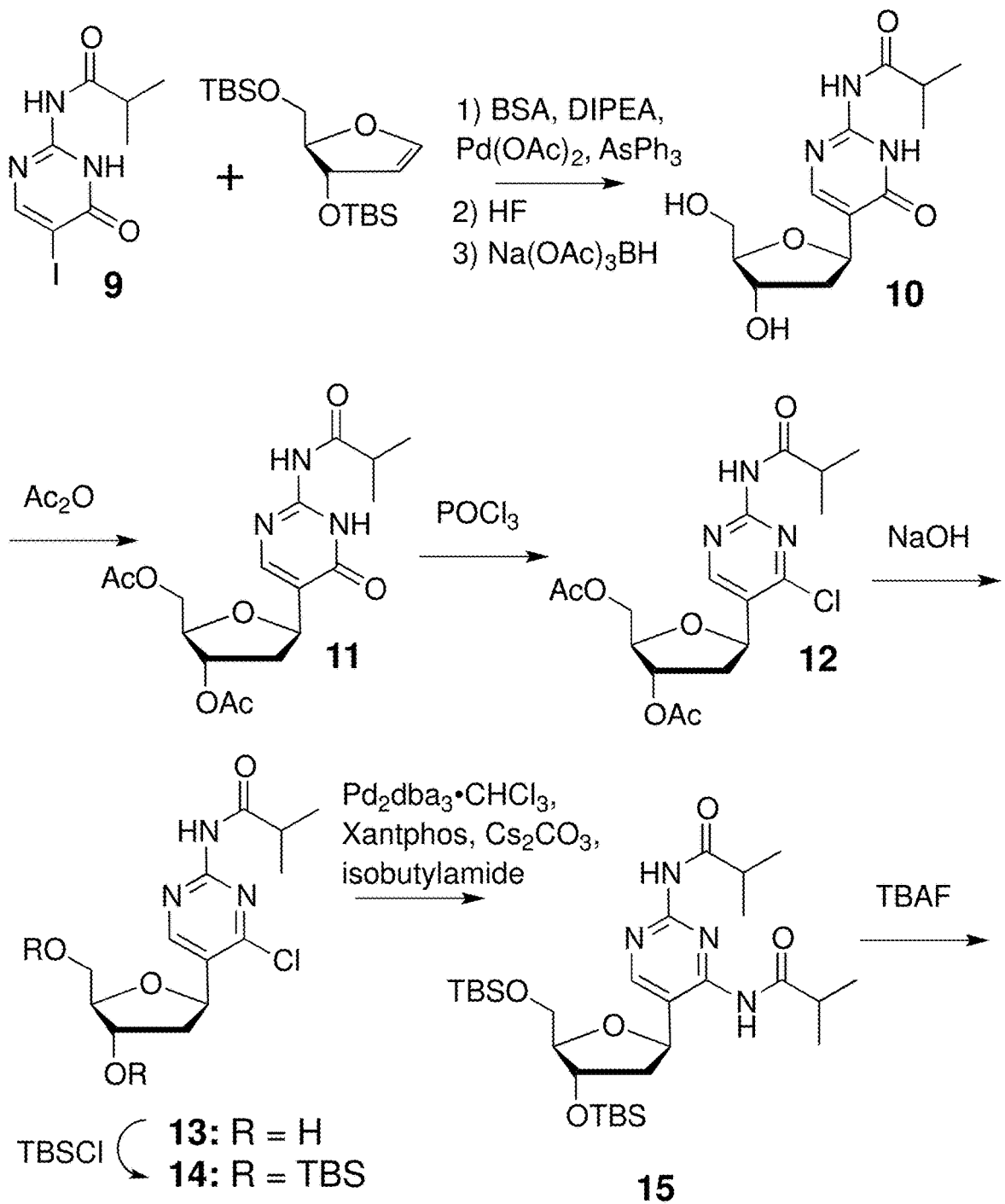

FIG. 5. Synthetic route to make the protected phosphoramidite carrying the small diamino-pyridine, which implements the donor-acceptor-donor K hydrogen bonding pattern. Part 1.

Figure 6:
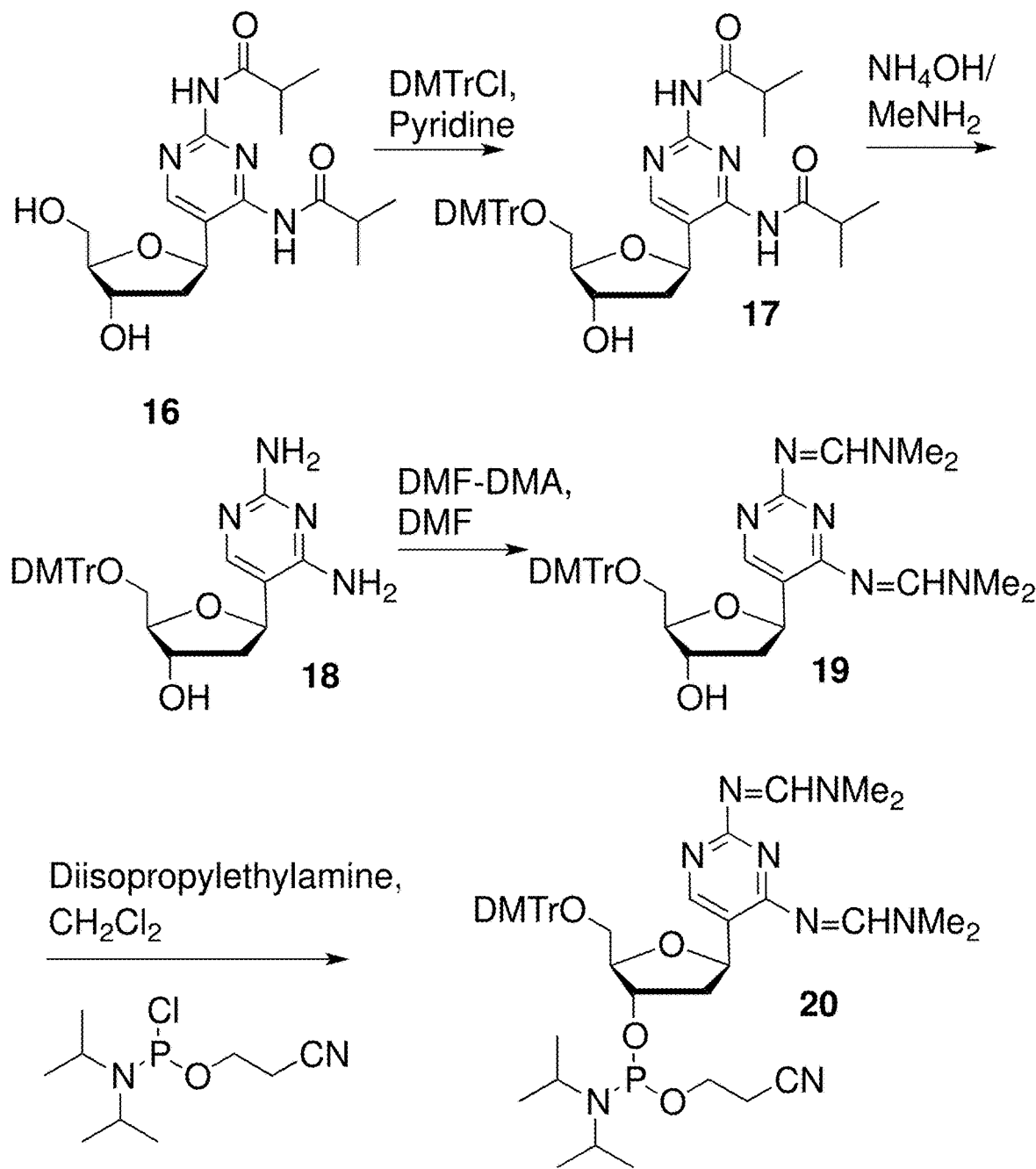

FIG. 6. Synthetic route to make the protected phosphoramidite carrying the small 2,4-diamino-pyrimidine, which implements the donor-acceptor-donor K hydrogen bonding pattern. Part 2.

Figure 7:
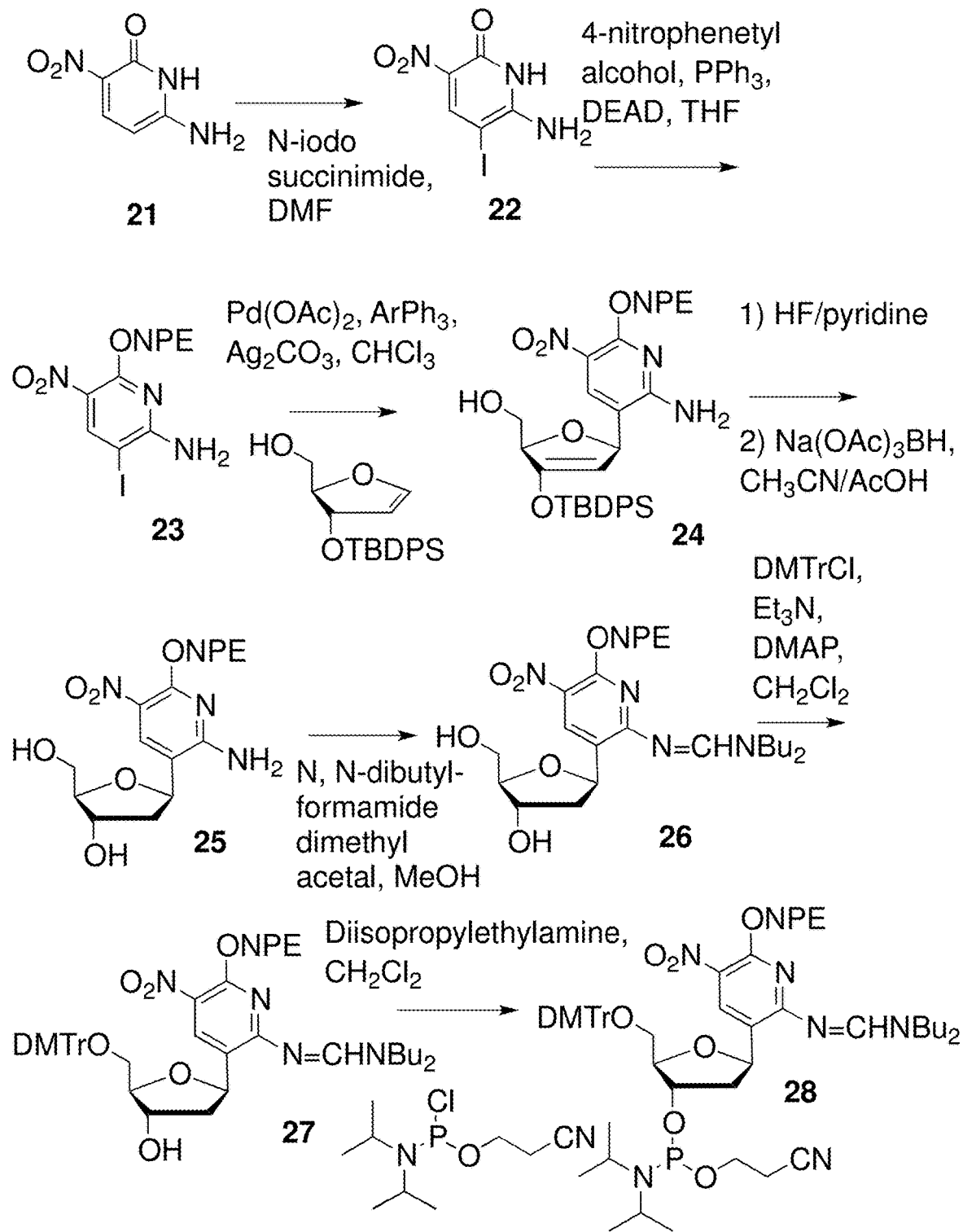

FIG. 7. Synthetic route to make the protected phosphoramidite for the 6-amino-3-nitropyridin-2-one heterocycle, implements the acceptor-donor-donor V hydrogen bonding pattern.

Figure 8:
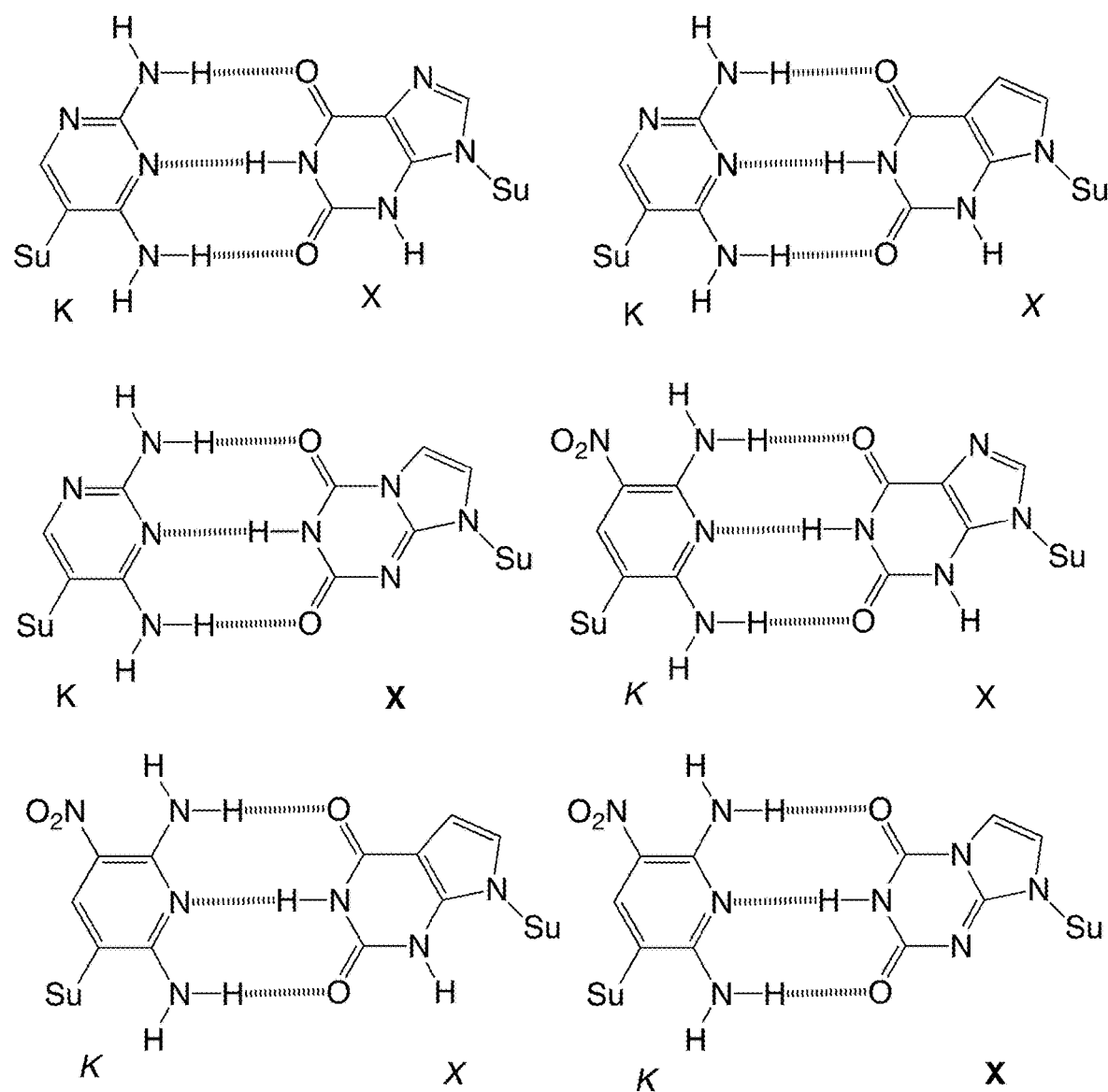

FIG. 8. Some non-standard purines and purine analogs that pair with some of the small pairs disclosed here, but with size complementarity. Note the two implementations of the donor-acceptor-donor K hydrogen bonding pattern. The implementation on 2,4-diaminopyrimidine is unitalicized K; the implementation on 2,6-diamino-3-nitropyridine is italicized K. In the size complementary Watson-Crick pairing shown here, its partner must present the acceptor-donor-acceptor X hydrogen bonding pattern. This is implemented in three deoxyribonucleosides: xanthosine (unitalicized, not bold X), 7-deazaxanthosine (italicized, not bold X), and 8H-1,3,5-triazine-2(8H)-4(3H)-dione (unitalicized, bold X). The same nomenclatures is used in the tables reporting reference melting temperatures.

FIG. 9. Structures of other Watson-Crick pairs on nucleobases nucleotides implementing various hydrogen bonding patterns. Su is the point of attachment of the indicated heterocycle to the oligonucleotide backbone.

Figure 10:
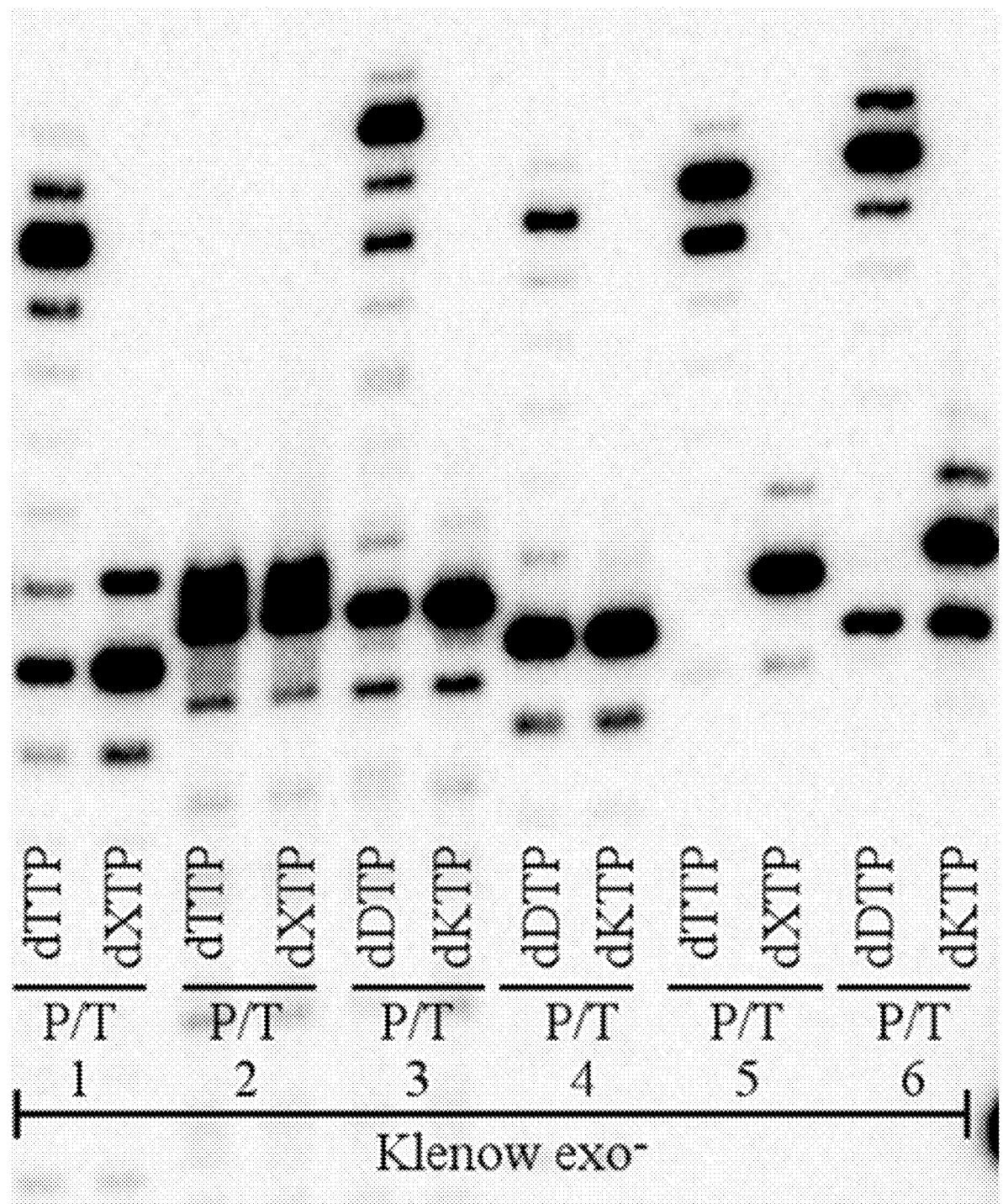

FIG. 10. Enzymatic extension primed with a skinny duplex. Extension to give Watson Crick size complementary pairs adds dTTP opposite template D. This gives extended product.

P/T1 (SKINNY PRIMER AND FAT TEMPLATE, A WATSON-CRICK SIZE COMPLEMENTARY INITIATOR)

Extension to give fat pairs would add dXTP to primer opposite template D. This does not give extended product.

```
                                              SEQ ID 43
        5'-KZZ TZS KTT KKS TST

SEQ ID 51
        3'-XPP DPB XDD XXB DBD DDD DDD
```

P/T2 (Fat Primer and Fat Template, a Fat Initiator)

Extension to give Watson Crick size complementary pairs adds dTTP opposite template D.

Extension to give fat pairs would add dXTP to primer opposite template D. This does not give extended product.

```
                                              SEQ ID 45
        5'-DBB XBP DXX DDP XPX

SEQ ID 51
        3'-XPP DPB XDD DBD DDD DDD
```

P/T3 (Fat Primer and Skinny Template, a Watson-Crick Size Complementary Initiator)

Extension to give Watson Crick size complementary pairs adds dDTP opposite template T. This gives extended product.

Extension to give skinny pairs would add dKTP to primer opposite template T. This does not give extended product.

```
                                              SEQ ID 45
        5'-DBB XBP DXX DDP XPX

SEQ ID 52
        3'-TSS KSZ TKK TTZ KZK TTT TTT
```

P/T4 (Skinny Primer and Skinny Template, a Skinny Initiator)

Extension to give Watson Crick size complementary pairs adds dDTP opposite template T. This gives extended product.

Extension to give skinny pairs would add dKTP to primer opposite template T. This does not give extended product.

```
                                              SEQ ID 43
        5'-KZZ TZS KTT KKS TST

SEQ ID 52
        3'-TSS KSZ TKK TTZ KZK TTT TTT
```

P/T5 (Skinny Primer and Fat Template, a Watson-Crick Size Complementary Initiator)

Extension to give Watson Crick size complementary pairs adds dTTP opposite template A. This gives extended product.

Extension to give fat pairs would add dXTP to primer opposite template A. This does not give extended product.

```
                                              SEQ ID 50
        5'-TCC TCC TTT TTC TCT

SEQ ID 53
        3'-AGG AGG AAA AAG AGA AAA AAA
```

P/T6 (Fat Primer and Skinny Template, a Watson-Crick Size Complementary Initiator).

Extension to give Watson Crick size complementary pairs adds dDTP opposite template T. This gives extended product.

Extension to give skinny pairs would add dKTP to primer opposite template T. This does not give extended product.

```
                                              SEQ ID 49
5'-AGG AGG AAA AAG AGA

SEQ ID 54
3'-TCC TCC TTT TTC TCT TTT TTT
```

DETAILED DESCRIPTION OF THE INVENTION

This invention comprises a process for forming a molecular complex comprising contacting a first oligonucleotide with a second oligonucleotide in aqueous solution, preferably between pH 5 and pH 9, and preferably between 0° C. and 100° C., and most preferably between 20° C. and 40° C., wherein the first oligonucleotide comprises a segment of nucleotides carrying heterocycles selected independently from those shown in FIG. 3, the second likewise comprises a segment of nucleotides carrying heterocycles selected independently from those shown in FIG. 3, and the sequences of these segments are complementary, wherein said complementary pairing is as shown in FIG. 3, hereinafter referred to as "skinny" pairs. The sequences of the two segments are such that the two skinny pairs are hydrogen bond complementary, in the sense that a hydrogen bond donor from one of the heterocycles is paired with a hydrogen bond acceptor from the other, as is exemplified in FIG. 3. This requires six heterocycles, each having six atoms in the ring, that implement the following hydrogen bonding patterns, written from top to bottom:

Donor-acceptor-donor (DAD): this hydrogen bonding pattern is abbreviated "K".

Donor-donor-acceptor (DDA): this hydrogen bonding pattern is abbreviated "Z".

Acceptor-donor-donor (ADD): this hydrogen bonding pattern is abbreviated "V".

Acceptor-donor-acceptor (ADA): this hydrogen bonding pattern is abbreviated "T".

Acceptor-acceptor-donor (AAD): this hydrogen bonding pattern is abbreviated "S".

Donor-acceptor-acceptor (DAA): this hydrogen bonding pattern is abbreviated "C".

According to the rules of molecular recognition taught in this disclosure, K pairs with T, Z pairs with S, and V pairs with C to form "skinny" pairs.

Another teaching at the instant disclosure is that different heterocyclic systems can implement the same hydrogen bonding pattern. For example, the ADA hydrogen bonding pattern "T" can be implemented on a uracil heterocycle, a thymine heterocycle, or a pseudo-uracil heterocycle, where the heterocycle is attached to the sugar (and the rest of the oligonucleotide chain). Likewise, the donor-acceptor-donor hydrogen bonding pattern K can be implemented by the 2,4-diaminopyrimidine heterocycle or by the 2,6-diamino-3-nitropyridine heterocycle. Synthesis of various of these heterocycles, when not previously known in the art, are given as examples.

Oligonucleotides are synthesized by solid phase DNA synthesis procedures well-known in the art. These syntheses are done using controlled pore glass as a support. Nucleotide building blocks are in the form of protected phosphoramidites, where the phosphorus carries preferably a diisopropylamino group and preferably a beta-cyanoethyloxy group.

The preferred protecting group on the 2,4-diaminopyrimidine heterocycle is N,N-dimethylformamidine. This implements the donor-acceptor-donor K hydrogen bonding pattern.

After nucleotide is synthesized, these are removed by treatment with ammonium hydroxide (concentrated, 55° C., approximately 16 hours).

The preferred protecting group on the N1-methyl-4-aminopyrimidin-2-one heterocycle, whose deprotected form implements the acceptor-acceptor-donor S hydrogen bonding pattern, is dialkylformamidine.

The preferred protecting group on 6-amino-5-nitropyridin-2-one heterocycle, whose deprotected form implements the acceptor-acceptor-donor Z hydrogen bonding pattern is nitrophenylethyl for the oxygen, and acetyl on the nitrogen.

The preferred protecting group on 6-amino-3-nitropyridin-2-one, whose deprotected form implements the acceptor-acceptor-donor V hydrogen bonding pattern is nitrophenylethyl for the oxygen, and dibutylformamidine on the nitrogen.

The protection of heterocycles implementing the T and C hydrogen bonding patterns, including thymine and cytosine, are well-known in the art.

The compositions of matter covered in the claims are bound species between a first oligonucleotide strand built from building blocks selected from the group K, T, Z, C, V and S, or some subset of these, where the sequence is independently pre-selected. This oligonucleotide is then bound to a second nucleotide also built from these building blocks, but with a sequence selected to be complementary to the first oligonucleotide strand when oriented antiparallel following the rules K pairs with T, Z pairs with S, and V pairs with C.

By "oligonucleotide", it is understood in the instant invention that these include species built from building blocks that comprise a single phosphate moiety, a 2'-deoxyribose moiety, and a heterocycle moiety, where the heterocycle is joined to carbon-1 of the 2'-deoxyribose moiety in the "beta" configuration, and the building blocks are linked via phosphodiester bonds. DNA is the archetypal form of an oligonucleotide, and the "skinny" pairs of the instant invention include the standard DNA pyrimidine nucleotides where the heterocycle is thymine and cytosine. However, in the instant invention, oligonucleotides may also comprise other heterocycles comprising a single ring with six atoms, including uracil, diaminopyrimidine, and others disclosed here. The only requirement is that the heterocycle be able to present three hydrogen bonding groups to a heterocycle that is paired on an antiparallel strand of another oligonucleotide, where the paired heterocycle has a complementary set of three hydrogen bonding groups. Further, the oligonucleotides of the instant invention may comprise other standard nucleobases guanine and adenine (although not in the regions forming skinny nucleobase pairs), as well as many of their analogs, including 7-deazaguanine and diaminopurine.

Further, the instant invention is not limited to compositions that have only two oligonucleotide strands. Three or more oligonucleotides may interact in the claimed compositions. The only limitation is that the inventive parts of these compositions are the segments of those oligonucleotides that interact with other segments via skinny pairs. Further, the instant invention also covers a single oligonucleotide that folds on itself so long as the fold is stabilized by two or more segments within that oligonucleotide that interact with each other via skinny pairs.

Well known in the art are nucleotide building blocks where the nucleobase heterocycle has appended to it a side chain that carries a functional group. For example, thymidine, which has a nucleobase that implements the T acceptor-donor-acceptor hydrogen bonding pattern, is available commercially that has its 5-methyl group replaced by an alkenyl linker or an alkynyl group, to which is appended an aliphatic chain comprising preferably one or two methylene ($CH_2$) units (is possibly more), to which is appended a functional group, preferably an amino group or a thiol group. A represented publication, which is incorporated in its entirety by reference is [Held, H. A., Benner, S. A. (2002) Challenging artificial genetic systems: Thymidine analogs with 5-position sulfur functionality. *Nucl. Acids Res.* 30, 3857-3869.]. A fluorescent tag may be appended to the amino or thiol group.

Likewise, similar tags are well-known in the art as commercial products with similarly derivatized or underivatized side chains appended to the analogous position of cytosine; these are used for sequencing using cyclic reversible termination architectures, the details of which are incorporated by reference. Likewise, various implementations of pyrimidine heterocycles that implement the S acceptor-acceptor-donor hydrogen bonding pattern can have the preferred methyl group at the analogous position replaced by an alkenyl linker or an alkynyl group, derivatized or underivatized.

This invention also comprises the duplexes that are formed by skinny pairing. It also comprises hairpins and other single-stranded structures where skinny pairs are formed within a single oligonucleotide.

Further, the instant invention has discovered that a skinny duplex can serve as a primer for certain DNA polymerases. Accordingly, the instant invention comprises the process by which a primer bound to a template by skinny base pairing is extended to form an elongated duplex where the extension comprises standard Watson-Crick base pairs.

EXAMPLES

Example 1. Implementation of the Donor-Acceptor-Donor Hydrogen Bonding Pattern on a 2,6-diamino-3-nitropyridine Heterocycle (FIG. 4)

Compound 2: A mixture of 2-amino-6-chloro-3-nitropyridine (1, 5.7 g, 32.8 mmol), water (4.5 mL), c-$H_2SO_4$ (1.26 mL) and $H_5IO_6$ (1.59 g) was stirred for 15 min at 95° C. Iodine (3.6 g) was added in portions. The reaction mixture was stirred for 1 h at 95° C., cooled to room temperature, poured into saturated aqueous sodium thiosulfate solution and extracted with ethyl acetate. The organic layer was dried ($Na_2SO_4$), filtered and concentrated. The residue was purified by silica gel column chromatography (Hex/EtOAc=3/2) to give compound 2 (8.7 g, 29.1 mmol, 88%). $^1$H NMR (DMSO-$d_6$, 300 MHz) delta8.62 (s, 1H), 8.26 (brs, 2H).

Compound 3: A solution of palladium acetate (187 mg, 0.83 mmol) and triphenyl arsine (509 mg, 1.66 mmol) in chloroform (30 mL) was stirred for 30 min at room temperature. This solution was added to the mixture of glycal (3.25 g, 9.2 mmol), 2 (2.49 g, 8.3 mmol) and silver carbonate (4.59 g, 16.6 mmol) in chloroform (60 mL) at room temperature. The reaction mixture was refluxed overnight, cooled to room temperature and filtered through a celite pad, the filtrate was concentrated and the residue was purified by silica gel column chromatography (Hex/EtOAc=4/1 to 7/3) to give compound 3 (2.75 g, 5.23 mmol, 63%) as an orange foam.

$^1$H NMR (CDCl$_3$, 300 MHz) delta8.42 (s, 1H), 7.73-7.82 (m, 4H), 7.41-7.48 (m, 6H), 5.83 (m, 1H), 7.77 (m, 1H), 4.23 (s, 1H), 3.90 (m, 2H), 1.78 (t, 1H, J=6.0), 1.23 (t, 1H, J=6.9), 1.08 (s, 9H).

Compound 5: To a stirred solution of 3 (2.75 g, 5.23 mmol) in THF (60 mL) as added AcOH (1.5 mL), followed by addition of IM TBAF in THF (7.9 mL) at 0° C. After 30 min stirring, the reaction mixture was concentrated to give crude compound 4, which was dissolved in $CH_3CN$/AcOH (46 mL/23 mL). To this mixture was added Na(OAc)$_3$BH (1.66 g, 7.83 mmol) at 0° C. After 1 h stirring at 0° C., acetone was added and the reaction mixture was concentrated. The residue was purified by silica gel column chromatography ($CH_2Cl_2$/MeOH=15/1) to give compound 5 (1.21 g, 4.18 mmol, 80%) as a yellow solid.

$^1$H NMR (DMSO-$d_6$, 300 MHz) delta8.49 (s, 1H), 8.14 (brs, 2H), 5.13 (d, 1H, J=3.9), 5.06 (dd, 1H, J=5.7, 9.9), 4.83 (t, 1H, J=5.4), 4.17 (m, 1H), 3.78 (m, 1H), 3.43-3.52 (m, 2H), 2.16 (dd, 1H, J=5.7, 12.6), 1.66 (m, 1H).

Compound 6: Compound 5 (1.2 g, 4.14 mmol) was dissolved in 7 N $NH_3$ in MeOH (80 mL) and heated overnight at 110° C. The reaction mixture cooled and concentrated. The residue was washed with ethanol/ether mixture to give compound 6 (1 g, 3.7 mmol, 90%) as a yellow solid.

$^1$H NMR (DMSO-$d_6$, 300 MHz) delta7.96 (s, 1H), 7.25 (brs, 4H), 5.01-5.15 (m, 2H), 4.88 (dd, 1H, J=6.3, 9.6), 4.20 (m, 1H), 3.74 (m, 1H), 3.47-3.58 (m, 2H), 1.89-1.97 (m, 2H)

$^{13}$C NMR (DMSO-$d_6$, 75 MHz) delta 160.6, 155.4, 133.7, 118.2, 112.7, 88.4, 78.1, 72.7, 62.1, 40.9.

Compound 7: To a stirred solution of 6 (310 mg, 1.15 mmole) in pyridine (20 mL) was added DMTCI (428 mg, 1.26 mmole) at room temperature. After being stirred at room temperature for 3 h, catalytic amounts of DMAP were added. The reaction mixture was stirred for additional 1 hour and concentrated. The residue was purified by silica gel column chromatography (Hex/EtOAc=1/2 to 1/4) to give compound 7 (410 mg, 0.72 mmole, 62%).

$^1$H-NMR (300 MHz, DMSO-$d_6$): delta 8.07 (s, 1H), 6.79-8.0 (m, 17H), 5.13 (d, 1H, J=3.9), 4.94 (dd, 1H, J=9.0, 6.0), 4.11 (m, 1H), 3.85 (m, 1H), 3.71 (s, 6H), 3.08 (d, 2H, J=3.6), 2.15 (m, 1H), 1.86 (m, 1H).

Compound 8: To a stirred solution of compound 7 (2.23 g, 3.9 mmole) in $CH_2Cl_2$ (80 mL) were added N,N-diisopropylethylamine (1.02 mL, 5.86 mmole) and 2-cyanoethyl N,N-diisopropylchloro phosphoramidite (1.13 mL, 5.1 mmole) at room temperature. The reaction mixture was stirred at room temperature for 30 min and extracted with water. The organic layer was dried ($Na_2SO_4$), filtered and concentrated. The residue was purified by neutral silica gel column chromatography (Hex/EtOAc=1/4) to give compound 8 (2.62 g, 3.4 mmole, 87%). $^1$H-NMR (300 MHz, CDCl$_3$): delta 8.10, 8.08 (2s, 1H), 6.80-7.35 (m, 13H), 5.00 (m, 1H), 4.70 (m, 1H), 4.11 (m, 2H), 3.79 (s, 6H), 3.36-3.67 (m, 5H), 2.62 (m, 1H), 2.42-2.56 (m, 2H), 2.05-2.29 (, 1H), 1.05-1.28 (m, 12H); $^{31}$P-NMR (120 MHz, CDCl$_3$): delta 149.8, 149.3.

Example 2. Implementation of the Donor-Acceptor-Donor Hydrogen Bonding Pattern on a 2,4-diaminopyrimidine Heterocycle (FIG. 5 and FIG. 6)

To synthesized protected K nucleoside, iodo-isocytosine derivative (9) was coupled with glycal and the resulting product was treated with HF/pyridine to give ketone, which was reduced with NaBH(OAc)$_3$ to give compound 10. The two free hydroxyl groups were protected with Ac$_2$O to give compound 11, which was treated with POCl$_3$ to give compound 12. Before displacing the chloride, the acetyls were replaced by TBS protecting groups by treating with NaOH to give 13, and reacting with TBDMS chloride to give the bis-silyl ether 14. Pd-catalyzed coupling reaction of 14 with the amide of isobutyric acid gave compound 15.

Moving on to FIG. 6, the TBDMS groups were removed using TBAF to give protected dK nucleoside 16. Following protection of the 5'-OH group as the DMT groups in 17, the protecting groups were exchanged to give dK phosphoramidite protected with N,N-dimethylformamidine groups. (FIG. 6). Isobutyroyl groups were removed from 17 by treatment with NH$_4$OH/CH$_3$NH$_2$ (1/1) to give the diamine 18. Protection of exocyclic diamino groups of 18 with N,N-dimethylformamide dimethyl acetal gave compound 19. Using standard conditions, 19 was converted to the corresponding phosphoramidite 20.

To determine whether this phosphoramidite 20 can be used for synthesis of oligonucleotide containing dK and dX, dK-dT dimer was synthesized using standard conditions, treated with the following conditions to remove the exocyclic amine protection group and analyzed by reverse HPLC. From HPLC analysis, 6% (condition a) and 15% (condition e) of mono protected are still remained, but most Dmf protection groups of dK can be removed under all these conditions.

Example 3. Synthesis of 2'-Deoxynucleoside with Heterocycle Implementing the V Hydrogen Bonding Pattern. (FIG. 7)

Compound 22: (6-Amino-5-iodo-3-nitro-2(1H)-pyridone). A mixture of 6-amino-3-nitropyridin-2-one (21 in FIG. 7, 5.0 g, 32.2 mmol) and N-iodosuccinimide (8.7 g, 38.6 mmol) in DMF (100 mL) was stirred at rt for 1 h. The mixture was poured into water (150 mL) and the precipitate was filtered and washed with methanol and dried to give 22 as a yellow solid (3.0 g, 33%). $^1$H NMR (300 MHz, DMSO-d$_6$) delta 8.51 (s, 1H), 7.4-7.6 (br s, 2H).

Compound 23: (3-Iodo-5-nitro-6-[2-(4-nitrophenyl)ethoxy]-2-pyridinamine) To a mixture of compound 22 (3.0 g, 10.7 mmol), 4-nitrophenetyl alcohol (2.68 g, 16.0 mmol) and triphenylphosphine (4.20 g, 16 mmol) in anhydrous THF (100 mL) was added diethylazodicarboxylate (2.5 mL, 16 mmol). The mixture was stirred at rt for 2 days and evaporated with silica gel. The residue was purified by flash chromatography (silica, hexanes:CH$_2$Cl$_2$=1:3) to give a yellow solid. It was dispersed in ethyl acetate/hexanes (20 mL/60 mL) and filtered and dried to give compound 23 (2.2 g, 48%). $^1$H NMR (300 MHz, CDCl$_3$) delta 8.59 (s, 1H), 8.17 (d, 2H, J=8.7 Hz), 7.52 (d, 2H, J=8.7 Hz), 5.47 (br s, 2H), 4.57 (t, 2H, J=6.3 Hz), 3.22 (t, 2H, J=6.3 Hz). HRMS (ESI) m/z calculated for C$_{13}$H$_{11}$IN$_4$O$_5$Na (M+Na)$^+$ 452.9672, found 452.9666, m/z calculated for C$_{13}$H$_{11}$IN$_4$O$_5$K (M+K)$^+$ 468.9411, found 468.9406.

Compound 25: (3-(2'-Deoxy-beta-D-ribofuranosyl)-5-nitro-6-[2-(4-nitrophenyl)ethoxy]-2-pyridinamine). Palladium acetate (132 mg, 0.6 mmol) and triphenylarsine (366 mg, 1.2 mmol) were dissolved in chloroform (20 mL), and the mixture was stirred at rt for 30 min. Then it was added to a mixture of compound 3 (2.58 g, 6.0 mmol), glycal (2.34 g, 6.6 mmol) and silver carbonate (3.31 g, 12.0 mmol) in chloroform (40 mL). The resulting mixture was refluxed overnight. After cooling to rt, it was filtered through Celite and washed with ethyl acetate. The combined filtrate was concentrated in vacuo. The residue was purified by flash chromatography (silica, ethyl acetate:hexanes=1:1) to give a brown solid (24).

This material, without further characterization, was dissolved in THF (50 mL) and treated with pyridine hydrofluoride (0.5 mL) and stirred at rt for 1 h. The mixture was evaporated with silica gel and the residue was purified by flash chromatography (silica, ethyl acetate) to give a yellow solid. This material was dissolved in acetic acid (20 mL) and acetonitrile (20 mL) and treated with sodium triacetoxyborohydride (1.48 g, 7.0 mmol) and stirred at rt for 2 h. The mixture was poured into brine (150 mL) and extracted with ethyl acetate. The combined organic layers were dried over Na$_2$SO$_4$, filtered and concentrated. The residue (25) was purified by flash chromatography (silica, ethyl acetate: MeOH=30:1) to give a yellow solid (800 mg, 32% for 3 steps). $^1$H NMR (300 MHz, CD$_3$OD) delta 8.14 (s, 1H), 8.13 (d, 2H, J=9.0 Hz), 7.59 (d, 2H, J=9.0 Hz), 5.02 (dd, 1H, J=11.1, 5.4 Hz), 4.63 (t, 2H, J=6.3 Hz), 4.37 (m, 1H), 3.92 (dd, 1H, J=5.7, 3.0 Hz), 3.72 (d, 2H, J=3.0 Hz), 3.20 (t, 2H, J=6.5 Hz), 2.22 (ddd, 1H, J=13.2, 11.4, 6.3 Hz), 2.00 (ddd, 1H, J=12.9, 7.2, 1.5 Hz).

Compound 26 (N-[(Dibutylamino)methylene]-3-(2'-deoxy-beta-D-ribofuranosyl)-5-nitro-6-[2-(4-nitrophenyl)ethoxy]-2-pyridinamine) A mixture of compound 25 (1.15 g, 2.74 mmol), and N,N-dibutylformamide dimethyl acetal (1.5 mL) in methanol (20 mL) was stirred at rt overnight. The mixture was evaporated and purified by flash chromatography (neutral silica, ethyl acetate:hexanes=2:1). The major fraction was collected and evaporated to give a compound 26 as a yellow solid (1.08 g, 70%). $^1$H NMR (300 MHz, CDCl$_3$) delta 8.51 (s, 1H), 8.38 (s, 1H), 8.14 (d, 2H, J=9.0 Hz), 7.53 (d, 2H, J=9.0 Hz), 5.40 (dd, 1H, J=9.3, 6.0 Hz), 4.62 (t, 2H, J=6.2 Hz), 4.38 (m, 1H), 3.96 (dd, 1H, J=8.4, 4.5 Hz), 3.75-3.9 (m, 2H), 3.53 (t, 2H, J=7.5 Hz), 3.36 (t, 2H, J=7.2 Hz), 3.23 (t, 2H, J=6.2 Hz), 2.40 (ddd, 1H, J=13.2, 6.0, 2.7 Hz), 1.8-1.9 (m, 1H), 1.55-1.7 (m, 4H), 1.3-1.4 (m, 4H), 0.96 (t, 3H, J=7.2 Hz), 0.95 (t, 3H, J=7.2 Hz). $^{13}$C NMR (75 MHz, CDCl$_3$) delta 160.42, 156.21, 155.48, 147.06, 146.65, 134.11, 130.44, 126.97, 123.83, 123.49, 86.95, 75.61, 73.86, 66.66, 63.61, 52.52, 46.36, 42.94, 35.54, 31.19, 29.40, 20.53, 19.91, 14.11, 13.86.

Compound 27: (N-[(Dibutylamino)methylene]-3-(2'-deoxy-5'-O-dimethoxytrityl-beta-D-ribofuranosyl)-5-nitro-6-[2-(4-nitrophenyl)ethoxy]-2-pyridinamine) A mixture of compound 26 (1.08 g, 1.93 mmol), dimethoxytrityl chloride (687 mg, 2.03 mmol), triethylamine (0.54 mL) and DMAP (5 mg) in dichloromethane (50 mL) was stirred at rt for 3 h. It was poured into water and extracted with dichloromethane. The combined organic layer was dried (Na$_2$SO$_4$), filtered and evaporated. The residue was purified by flash chromatography (neutral silica, ethyl acetate:hexanes=1:2) to give a compound 17 as a yellow solid (1.50 g, 90%). $^1$H NMR (300 MHz, CDCl$_3$) delta 8.51 (s, 1H), 8.42 (s, 1H), 8.16 (d, 2H, J=8.7 Hz), 7.54 (d, 2H, J=9.0 Hz), 7.2-7.9 (m, 9H), 6.84 (dd, 4H, J=9.0, 1.2 Hz), 5.39 (dd, 1H, J=9.3, 6.0 Hz), 4.62 (t, 2H, J=6.3 Hz), 4.30 (m, 1H), 4.02 (m, 1H), 3.79 (s, 6H), 3.2-3.6 (m, 8H), 2.42 (ddd, 1H, J=12.9, 5.7, 2.4 Hz), 1.55-1.9 (m, 4H), 1.3-1.4 (m, 4H), 0.96 (t, 3H, J=7.2 Hz), 0.95 (t, 3H, J=7.2 Hz). $^{13}$C NMR (75 MHz, CDCl$_3$) delta 159.99, 158.71, 155.91, 155.31, 147.04, 146.66, 145.02, 136.11, 136.01, 133.90, 130.43, 130.29, 128.31, 128.08, 127.15, 127.02, 124.13, 123.81, 113.38, 86.51, 85.70, 75.33, 74.90, 66.58, 64.74, 55.44, 52.45, 46.33, 42.50, 35.54, 31.20, 29.38, 20.54, 19.90, 14.10, 13.85.

Example 4. Synthesis of Oligonucleotides

Support-bound oligonucleotides were synthesized on an Applied BioSystems 394 DNA synthesizer using the following phosphoramidite building blocks (P, Z, S, K, K and X (italicized "K" represents 2,6-diamino-3-nitro-5-(1'-beta-D-2'-deoxyribofuranosyl)-pyridine; non-italicized K represents 2,6-diamino-3-(1'-beta-D-2'-deoxyribofuranosyl)-pyrimidine. Italicized "X" represents 2'-deoxy-7-deazaxanthosine; non-italicized "X" represents 2'-deoxy-7-xanthosine) phosphoramidites from Firebird Biomolecular Sciences), (2: 2-Aminopurine-CE Phosphoramidite, D: Pac-2-Amino-dA-CE Phosphoramidite, B: dmf-isodG-CE Phosphoramidite, X: dX-CE Phosphoramidite, X: 7-deaza-dX-CE Phosphoramidite, t: 2-Thio-dT-CE Phosphoramidite and standard Ultramild CE phosphoramidites from Glen Research) and Ultramild CPG supports (Glen Research) at a 1.0 µmol scale following the standard procedure. Each phosphoramidite unit was used at a concentration of 0.1 M in dry $CH_3CN$; coupling times were 10 min for each step. After completion of the synthesis, 1) The CPG support with oligonucleotides with X or Z was treated with 1.0 M DBU in dry $CH_3CN$ (2.0 mL) for 24 hours. Then the CPG was washed with $CH_3CN$ and dried. The dried CPG was treated with $NH_4OH$ (1.0 mL) for 16 h at 55° C.; support was removed by filtration.

2) The CPG support having oligonucleotides containing 2-thioT or X was treated with $NH_4OH$ (1.0 mL) for 16 hours at room temperature, and the support was removed by filtration.

3) The CPG support having oligonucleotides containing the other nucleobases was treated with $NH_4OH$ (1.0 mL) for 16 hours at 55° C., and the support was removed by filtration.

The filtrate was lyophilized and the residue was purified on ion-exchange HPLC.

Example 5. Measurement of Melting Temperatures

Melting temperatures ($T_m$) were measured in a reaction containing 2.0 µM of each oligonucleotide dissolved in buffer (10 mM NaCl, 10 mM sodium cacodylate, pH 6.8). Absorbance was monitored on a Shimadzu UV-Vis Spectrophotometer at 260 nm over a temperature range of 20.0° C. to 90.0° C. with a change in temperature of 0.5° C. per min. The $T_m$ values were determined by averaging the temperatures of the three heating measurements.

To demonstrate the surprising and unexpected pairing potential between two oligonucleotides with the pairs are skinny, the series of melting temperatures were run. Each experiment was run in 10 mM Na cacodylate buffer (pH 6.8) containing 10 mM NaCl. Each oligonucleotide was present at 2 µM concentrations. These studies were done using a systematically varied set of reference 15mers.

Example 5.1: Watson-Crick Base Size Complementary Reference Pairing

The initial experiments are reference experiments that show the melting temperatures of the reference 15mer duplex where size complementarity rules are followed as well as hydrogen bonding complementarity rules. The acceptor-donor-acceptor hydrogen bonding pattern on the large component of the pair was implemented on 7-deazaxanthine. The donor-acceptor-donor hydrogen bonding pattern on the small component was implemented by 2,6-diamino-3-nitropyridine. The acceptor-acceptor-donor hydrogen bonding pattern on the small component is implemented by methylpseudocytidine. The bond donor-donor-acceptor hydrogen bonding pattern implemented on the large complement is implemented by isoguanine. The structures for the other pairs are shown in FIG. 9. Data are in Table 1.

TABLE 1

Watson-Crick reference pairs.

| | | |
|---|---|---|
| 5'-CGTCGCCCCCGGCTC-3'<br>3'-GCAGCGGGGGCCGAG-5' | SEQ ID 1<br>SEQ ID 2 | 56.3<br>In both of these sequences, only standard nucleotides are present. |
| 5'-CGTCGTTTTTGGCTC-3'<br>3'-GCAGCAAAAACCGAG-5' | SEQ ID 3<br>SEQ ID 4 | 48.3<br>In both of these sequences, only standard nucleotides are present. |
| 5'-CGTCGTTPTTGGCTC-3'<br>3'-GCAGCAAZAACCGAG-5' | SEQ ID 5<br>SEQ ID 6 | 52.0<br>The letter "P" represents 7-amino-9-(1'-beta-D-2'-deoxyribofuranosyl)-imidazo[1,2-c]pyrimidin-5(1H)-one; the letter "Z" represents 6-amino-3-(2'-deoxy-D-ribofuranosyl)-5-nitro-1H-pyridin-2-one. |
| 5'-CGTCGTPPPTGGCTC-3'<br>3'-GCAGCAZZZACCGAG-5' | SEQ ID 7<br>SEQ ID 8 | 63.7<br>The letter "P" represents 7-amino-9-(1'-beta-D-2'-deoxyribofuranosyl)-imidazo[1,2-c]pyrimidin-5(1H)-one; the letter "Z" represents 6-amino-3-(2'-deoxy-D-ribofuranosyl)-5-nitro-1H-pyridin-2-one. |
| 5'-CGTCGPTPTPGGCTC-3'<br>3'-GCAGCZAZAZCCGAG-5' | SEQ ID 9<br>SEQ ID 10 | 63.3<br>The letter "P" represents 7-amino-9-(1'-beta-D-2'-deoxyribofuranosyl)-imidazo[1,2-c]pyrimidin-5(1H)-one; the letter "Z" represents 6-amino-3-(2'-deoxy-D-ribofuranosyl)-5-nitro-1H-pyridin-2-one. |
| 5'-CGTCGPPPPPGGCTC-3'<br>3'-GCAGCZZZZZCCGAG-5' | SEQ ID 11<br>SEQ ID 12 | 75.7<br>The letter "P" represents 7-amino-9-(1'-beta-D-2'-deoxyribofuranosyl)-imidazo[1,2-c]pyrimidin-5(1H)-one; the letter "Z" represents 6-amino- |

TABLE 1-continued

Watson-Crick reference pairs.

| | | |
|---|---|---|
| | | 3-(2'-deoxy-D-ribofuranosyl)-5-nitro-1H-pyridin-2-one. |
| 5'-CGTCGTTSTTGGCTC-3'<br>3'-GCAGCAABAACCGAG-5' | SEQ ID 13<br>SEQ ID 14 | 49.8<br>The letter "S" represents 4-amino-N$^1$-methyl-5-(1'-beta-D-2'-deoxyribofuranosyl)-2(1H)-pyrimidinone; the letter "B" represents 4-amino-3-hydro-7-(2-deoxy-beta-D-ribofuranosyl)pyrrolo[2,3-d]pyrimidin-2-one. |
| 5'-CGTCGTSSSTGGCTC-3'<br>3'-GCAGCABBBACCGAG-5' | SEQ ID 15<br>SEQ ID 16 | 54.9<br>The letter "S" represents 4-amino-N$^1$-methyl-5-(1'-beta-D-2'-deoxyribofuranosyl)-2(1H)-pyrimidinone; the letter "B" represents 4-amino-3-hydro-7-(2-deoxy-beta-D-ribofuranosyl)pyrrolo[2,3-d]pyrimidin-2-one. |
| 5'-CGTCGSTSTSGGCTC-3'<br>3'-GCAGCBABABCCGAG-5' | SEQ ID 17<br>SEQ ID 18 | 55.7<br>The letter "S" represents 4-amino-N$^1$-methyl-5-(1'-beta-D-2'-deoxyribofuranosyl)-2(1H)-pyrimidinone, the letter "B" represents 4-amino-3-hydro-7-(2-deoxy-beta-D-ribofuranosyl)pyrrolo[2,3-d]pyrimidin-2-one. |
| 5'-CGTCGSSSSSGGCTC-3'<br>3'-GCAGCBBBBBCCGAG-5' | SEQ ID 19<br>SEQ ID 20 | 61.0<br>The letter "S" represents 4-amino-N$^1$-methyl-5-(1'-beta-D-2'-deoxyribofuranosyl)-2(1H)-pyrimidinone' the letter "B" represents 4-amino-3-hydro-7-(2-deoxy-beta-D-ribofuranosyl)pyrrolo[2,3-d]pyrimidin-2-one. |
| 5'-CGTCGTTXTTGGCTC-3'<br>3'-GCAGCAAKAACCGAG-5' | SEQ ID 21<br>SEQ ID 22 | 49.1<br>The letter "K" represents 2,6-diamino-3-nitro-5-(1'-beta-D-2'-deoxyribofuranosyl)-pyridine; the letter "X" represents 2'-deoxy-7-deazaxanthosine. |
| 5'-CGTCGTXXXTGGCTC-3'<br>3'-GCAGCAKKKACCGAG-5' | SEQ ID 23<br>SEQ ID 24 | 56.0<br>The letter "K" represents 2,6-diamino-3-nitro-5-(1'-beta-D-2'-deoxyribofuranosyl)-pyridine; the letter "X" represents 2'-deoxy-7-deazaxanthosine. |
| 5'-CGTCGXTXTXGGCTC-3'<br>3'-GCAGCKAKAKCCGAG-5' | SEQ ID 25<br>SEQ ID 26 | 53.1<br>The letter "K" represents 2,6-diamino-3-nitro-5-(1'-beta-D-2'-deoxyribofuranosyl)-pyridine; the letter "X" represents 2'-deoxy-7-deazaxanthosine. |
| 5'-CGTCGXXXXXGGCTC-3'<br>3'-GCAGCKKKKKCCGAG-5' | SEQ ID 27<br>SEQ ID 28 | 57.9<br>The letter "K" represents 2,6-diamino-3-nitro-5-(1'-beta-D-2'-deoxyribofuranosyl)-pyridine; the letter "X" represents 2'-deoxy-7-deazaxanthosine. |

TABLE 2

Watson-Crick reference pairs to compare different implementations of K and X hydrogen bonding patterns.

| | | |
|---|---|---|
| 5'-CGTCGTTXTTGGCTC-3'<br>3'-GCAGCAAKAACCGAG-5' | SEQ ID 29<br>SEQ ID 30 | 45.7<br>The letter "K" represents 2,4-diamino-5-(1'-beta-D-2'-deoxyribofuranosyl)-pyrimidine; the letter "X" represents 8-(beta-D-2'-deoxyribofuranosyl)imidazo[1,2-a]-1,3,5-triazine-2(8H)-4(3H)-dione. |
| 5'-CGTCGTTXTTGGCTC-3'<br>3'-GCAGCAAKAACCGAG-5' | SEQ ID 31<br>SEQ ID 30 | 48.6<br>The letter "K" represents 2,4-diamino-5-(1'-beta-D-2'-deoxyribofuranosyl)-pyrimidine; the letter "X" represents 2'-deoxyxanthosine. |
| 5'-CGTCGTTXTTGGCTC-3'<br>3'-GCAGCAAKAACCGAG-5' | SEQ ID 21<br>SEQ ID 30 | 50.5<br>The letter "K" represents 2,4-diamino-5-(1'-beta-D-2'-deoxyribofuranosyl)-pyrimidine; the letter "X" represents 2'-deoxy-7-deazaxanthosine. |

TABLE 2-continued

Watson-Crick reference pairs to compare different implementations of K and X hydrogen bonding patterns.

| | | |
|---|---|---|
| 5'-CGTCGTTXTTGGCTC-3'<br>3'-GCAGCAA*K*AACCGAG-5' | SEQ ID 29<br>SEQ ID 22 | 42.0<br>The letter "*K*" represents 2,6-diamino-3-nitro-5-(1'-beta-D-2'-deoxyribofuranosyl)-pyridine; the letter "X" represents 8-(beta-D-2'-deoxyribofuranosyl)imidazo[1,2-a]-1,3,5-triazine-2(8H)-4(3H)-dione. |
| 5'-CGTCGTTXTTGGCTC-3'<br>3'-GCGCAA*K*AACCGAG-5' | SEQ ID 31<br>SEQ ID 22 | 45.3<br>The letter "*K*" represents 2,6-diamino-3-nitro-5-(1'-beta-D-2'-deoxyribofuranosyl)-pyridine; the letter "X" represents 2'-deoxyxanthosine. |
| 5'-CGTCGTTXTTGGCTC-3'<br>3'-GCAGCAA*K*AACCGAG-5' | SEQ ID 21<br>SEQ ID 22 | 49.1<br>The letter "*K*" represents 2,6-diamino-3-nitro-5-(1'-beta-D-2'-deoxyribofuranosyl)-pyridine; the letter "X" represents 2'-deoxy-7-deazaxanthosine. |
| 5'-CGTCGTXXXTGGCTC-3'<br>3'-GCAGCAKKKACGAG-5' | SEQ ID 32<br>SEQ ID 33 | 37.1<br>The letter "K" represents 2,4-diamino-5-(1'-beta-D-2'-deoxyribofuranosyl)-pyrimidine; the letter "X" represents 8-(beta-D-2'-deoxyribofuranosyl)imidazo[1,2-a]-1,3,5-triazine-2(8H)-4(3H)-dione. |
| 5'-CGTCGTXXXTGGXTX-3'<br>3'-GCAGCAKKKACCGAG-5' | SEQ ID 34<br>SEQ ID 33 | 50.7<br>The letter "K" represents 2,4-diamino-5-(1'-beta-D-2'-deoxyribofuranosyl)-pyrimidine; the letter "X" represents 2'-deoxyxanthosine. |
| 5'-CGTCGTXXXTGGCTC-3'<br>3'-GCAGCAKKKACCGAG-5' | SEQ ID 23<br>SEQ ID 33 | 55.6<br>The letter "K" represents 2,4-diamino-5-(1'-beta-D-2'-deoxyribofuranosyl)-pyrimidine; the letter "X" represents 2'-deoxy-7-dezaxanthosine. |
| 5'-CGTCGTXXXTGGCTC-3'<br>3'GCAGCA*KKK*ACCGAG-5' | SEQ ID 32<br>SEQ ID 24 | 39.8<br>The letter "*K*" represents 2,6-diamino-3-nitro-5-(1'-beta-D-2'-deoxyribofuranosyl)-pyridine; the letter "X" represents 8-(beta-D-2'-deoxyribfuranosyl)imidazo[1,2-a]-1,3,5-triazine-2(8H)-dione. |
| 5'-CGTCGTXXXTGGCTC-3'<br>3'-GCAGCA*KKK*ACCGAG-5' | SEQ ID 34<br>SEQ ID 24 | 46.7<br>The letter "*K*" represents 2,6-diamino-3-nitro-5-(1'-beta-D-2'-deoxyribofuranosyl)-pyridine; the letter "X" represents 2'-deoxyxanthosine. |
| 5'-CGTCGTXXXTGGXTX-3'<br>3'-GCAGCA*KKK*ACCGAG-5' | SEQ ID 23<br>SEQ ID 24 | 56.0<br>The letter "*K*" represents 2,6-diamino-3-nitro-5-(1'-beta-D-2'-deoxyribofuranosyl)-pyridine; the letter "X" represents 2'-deoxy-7-deazaxanthosine. |
| 5'-CGTCGXTXTXGGCTC-3'<br>3'-GCAGCKAKAKCCGAG-5' | SEQ ID 35<br>SEQ ID 36 | 44.2<br>The letter "K" represents 2,4-diamino-5-(1'-beta-D-2'-deoxyribofuranosyl)-pyrimidine; the letter "X" represents 8-(beta-D-2'-deoxyribfuranosyl)imidazo[1,2-a]-1,3,5-triazine-2(8H)-4(3H)-dione. |
| 5'-CGTCGXTXTXGGCTC-3'<br>3'-GCAGCKAKAKCCGAG-5' | SEQ ID 37<br>SEQ ID 36 | 50.0<br>The letter "K" represents 2,4-diamino-5-(1'-beta-D-2'-deoxyribofuranosyl)-pyrimidine; the letter "X" represents 2'-deoxyxanthosine. |
| 5'-CGTCGXTXTXGGCTC-3'<br>3'-GCAGCKAKAKCCGAG-5' | SEQ ID 25<br>SEQ ID 36 | 57.7<br>The letter "K" represents 2,4-diamino-5-(1'-beta-D-2'-deoxyribofuranosyl)-pyrimidine; the letter "X" represents 2'-deoxy-7-deazaxanthosine. |
| 5'-CGTCGXTXTXGGCTC-3'<br>3'-GCAGC*K*A*K*A*K*CCGAG-5' | SEQ ID 35<br>SEQ ID 26 | 41.9<br>The letter "*K*" represents 2,6-diamino-3-nitro-5-(1'-beta-D-2'-deoxyribofuranosyl)-pyridine; the letter "X" represents 8-($\beta$-D-2'-deoxyribfuranosyl)imidazo[1,2-a]-1,3,5-triazine-2(8H)-4(3H)-dione. |

TABLE 2-continued

Watson-Crick reference pairs to compare different implementations of K and X hydrogen bonding patterns.

| Sequence | SEQ ID | Tm / Notes |
|---|---|---|
| 5'-CGTCG*X*T*X*TXGGCTC-3'<br>3'-GCAGC*KA*K*A*KCCGAG-5' | SEQ ID 37<br>SEQ ID 26 | 44.3<br>The letter "*K*" represents 2,6-diamino-3-nitro-5-(1'-beta-D-2'-deoxyribofuranosyl)-pyridine; the letter "X" represents 2'-deoxyxanthosine. |
| 5'-CGTCG*XTXTX*GGCTC-3'<br>3'-GCAGC*KAKAK*CCGAG-5' | SEQ ID 25<br>SEQ ID 26 | 53.1<br>The letter "*K*" represents 2,6-diamino-3-nitro-5-(1'-beta-D-2'-deoxyribofuranosyl)-pyridine; the letter "*X*" represents 2'-deoxy-7-deazaxanthosine. |
| 5'-CGTCGXXXXXGGCTC-3'<br>3'-GCAGCKKKKKCCGAG-5' | SEQ ID 38<br>SEQ ID 39 | 30.9<br>The letter "K" represents 2,4-diamino-5-(1'-beta-D-2'-deoxyribofuranosyl)-pyrimidine; the letter "X" represents 8-(beta-D-2'-deoxyribfuranosyl)imidazo[1,2-a]-1,3,5-triazine-2(8H)-4(3H)-dione. |
| 5'-CGTCG*XXXXX*GGCTC-3'<br>3'-GCAGCKKKKKCCGAG-5' | SEQ ID 40<br>SEQ ID 39 | 51.4<br>The letter "K" represents 2,4-diamino-5-(1'-beta-D-2'-deoxyribofuranosyl)-pyrimidine; the letter X" represents 2'-deoxyxanthosine. |
| 5'-CGTCG*XXXXX*GGCTC-3'<br>3'-GCAGCKKKKKCCGAG-5' | SEQ ID 27<br>SEQ ID 39 | 57.9<br>The letter "K" represents 2,4-diamino-5-(1' beta-D-2'-deoxyribofuranosyl)-pyrimidine; the letter "*X*" represents 2'-deoxy-7-deazaxanthosine. |
| 5'-CGTCGXXXXXGGCTC-3'<br>3'-GCAGCKKKKKCCGAG-5' | SEQ ID 38<br>SEQ ID 28 | 31.47<br>The letter "*K*" represents 2,6-diamino-3-nitro-5-(1'-beta-D-2'-deoxyribofuranosyl)-pyridine; the letter "X" represents 8-(β-D-2'-deoxyribfuranosyl)imidazo[1,2-a]-1,3,5-triazine-2(8H)-4(3H)-dione. |
| 5'-CGTCG*XXXXX*GGCTC-3'<br>3'-GCAGC*KKKKK*CCGAG-5' | SEQ ID 40<br>SEQ ID 28 | 44.7<br>The letter "*K*" represents 2,6-diamino-3-nitro-5-(1'-beta-D-2'-deoxyribofuranosyl)-pyridine; the letter "X" represents 2'-deoxyxanthosine. |
| 5'-CGTCG*XXXXX*GGCTC-3'<br>3'-GCAGC*KKKKK*CCGAG-5' | SEQ ID 27<br>SEQ ID 28 | 57.9<br>The letter "*K*" represents 2,6-diamino-3-nitro-5-(1'-beta-D-2'-deoxyribofuranosyl)-pyridine; the letter "*X*" represents 2'-deoxy-7-deazaxanthosine. |

Example 5.2

Comparison of two implementations of the small donor-acceptor-donor hydrogen bonding pattern, on 2,4-diaminopyrimidine versus 2,6-diamino-3-nitropyridine, and two implementations of the large the hydrogen bonding heterocycle implementing the acceptor-donor-acceptor hydrogen bonding pattern, in Watson-Crick base pairs. Data are shown in Table 2, where K is 2,4-diaminopyrimidine, italicized K is 2,6-diamino-3-nitropyridine, X is xanthosine, bold X is triazine, and italicized X is 7-dezazxanthosine

Example 5.3

Melting temperatures of the reference duplex where the middle five base pairs are skinny. Here, the implementation of the acceptor-acceptor-donor (S) hydrogen bonding pattern is on pseudocytidine.

TABLE 3

Mispairing in the skinny series gives less stable duplexes than the hydrogen bond matched skinny pairs, showing molecular recognition and its specificity.

| Sequence | SEQ ID | Tm / Notes |
|---|---|---|
| 5'-CGTCGTTTTTGGCTC-3'<br>3'-GCAGCAAZAACCGAG-5' | SEQ ID 3<br>SEQ ID 6 | 38.1<br>The letter "Z" represents 6-amino-3-(2'-deoxy-D-ribofuranosyl)-5-nitro-1H-pyridin-2-one. |
| 5'-CGTCGTTSTTGGCTC-3'<br>3'-GCAGCAAZAACCGAG-5' | SEQ ID 13<br>SEQ ID 6 | 47.2<br>The letter "Z" represents 6-amino-3-(2'-deoxy-D-ribofuranosyl)-5-nitro-1H-pyridin-2-one. The letter "S" represents 4-amino-N1-methyl-5-(1'-beta-D-2'-deoxyribofuranosyl)-2(1H)-pyrimidinone. |
| 5'-CGTCGTSSSTGGCTC-3'<br>3'-GCAGCAZZZACCGAG-5' | SEQ ID 15<br>SEQ ID 8 | 54.1<br>The letter "Z" represents 6-amino-3-(2'-deoxy-D-ribofuranosyl)-5-nitro-1H-pyridin-2-one. |

TABLE 3-continued

Mispairing in the skinny series gives less stable duplexes than the hydrogen bond matched skinny pairs, showing molecular recognition and its specificity.

| | | | |
|---|---|---|---|
| | | | The letter "S" represents 4-amino-N1-methyl-5-(1'-beta-D-2'-deoxyribofuranosyl)-2(1H)-pyrimidinone. |
| 5'-CGTCGSTSTSGGCTC-3'<br>3'-GCAGCZAZAZCCGAG-5' | SEQ ID 17<br>SEQ ID 10 | 50.1 | The letter "Z" represents 6-amino-3-(2'-deoxy-D-ribofuranosyl)-5-nitro-1H-pyridin-2-one.<br>The letter "S" represents 4-amino-N1-methyl-5-(1'-beta-D-2'-deoxyribofuranosyl)-2(1H)-pyrimidinone. |
| 5'-CGTCGTTTTTGGCTC-3'<br>3'-GCAGCZZZZZCCGAG-5' | SEQ ID 3<br>SEQ ID 12 | <20 | The letter "Z" represents 6-amino-3-(2'-deoxy-D-ribofuranosyl)-5-nitro-1H-pyridin-2-one. |
| 5'-CGTCGTTSTTGGCTC-3'<br>3'-GCAGCZZZZZCCGAG-5' | SEQ ID 13<br>SEQ ID 12 | <20 | The letter "Z" represents 6-amino-3-(2'-deoxy-D-ribofuranosyl)-5-nitro-1H-pyridin-2-one.<br>The letter "S" represents 4-amino-N1-methyl-5-(1'-beta-D-2'-deoxyribofuranosyl)-2(1H)-pyrimidinone. |
| 5'-CGTCGTSSSTGGCTC-3'<br>3'-GCAGCZZZZZCCGAG-5' | SEQ ID 15<br>SEQ ID 12 | 37.4 | The letter "Z" represents 6-amino-3-(2'-deoxy-D-ribofuranosyl)-5-nitro-1H-pyridin-2-one.<br>The letter "S" represents 4-amino-N1-methyl-5-(1'-beta-D-2'-deoxyribofuranosyl)-2(1H)-pyrimidinone. |
| 5'-CGTCGSTSTSGGCTC-3'<br>3'-GCAGCZZZZZCCGAG-5' | SEQ ID 17<br>SEQ ID 12 | 36.3 | The letter "Z" represents 6-amino-3-(2'-deoxy-D-ribofuranosyl)-5-nitro-1H-pyridin-2-one.<br>The letter "S" represents 4-amino-N1-methyl-5-(1'-beta-D-2'-deoxyribofuranosyl)-2(1H)-pyrimidinone. |
| 5'-CGTCGSSSSSGGCTC-3'<br>3'-GCAGCZZZZZCCGAG-5' | SEQ ID 19<br>SEQ ID 12 | 60.9 | The letter "Z" represents 6-amino-3-(2'-deoxy-D-ribofuranosyl)-5-nitro-1H-pyridin-2-one.<br>The letter "S" represents 4-amino-N1-methyl-5-(1'-beta-D-2'-deoxyribofuranosyl)-2(1H)-pyrimidinone. |
| 5'-CGTCGTTTTTGGCTC-3'<br>3'-GCAGCAAZAACCGAG-5' | SEQ ID 3<br>SEQ ID 6 | 38.1 | The letter "Z" represents 6-amino-3-(2'-deoxy-D-ribofuranosyl)-5-nitro-1H-pyridin-2-one. |
| 5'-CGTCGTTTTTGGCTC-3'<br>3'-GCAGCAAKAACCGAG-5' | SEQ ID 3<br>SEQ ID 22 | 45.9 | The letter "K" represents 2,6-diamino-3-nitro-5-(1'-beta-D-2'-deoxyribofuranosyl)-pyridine. |
| 5'-CGTCGTTSTTGGCTC-3'<br>3'-GCAGCAAKAACCGAG-5' | SEQ ID 13<br>SEQ ID 22 | 37.6 | The letter "K" represents 2,6-diamino-3-nitro-5-(1'-beta-D-2'-deoxyribofurarosyl)-pyridine.<br>The letter "S" represents 4-amino-N1-methyl-5-(1'-beta-D-2'-deoxyribofuranosyl)-2(1H)-pyrimidinone. |
| 5'-CGTCGTTTTTGGCTC-3'<br>3'-GCAGCAKKKACCGAG-5' | SEQ ID 3<br>SEQ ID 24 | 48.0 | The letter "K" represents 2,6-diamino-3-nitro-5-(1'-beta-D-2'-deoxyribofuranosyl)-pyridine. |
| 5'-CGTCGTSSSTGGCTC-3'<br>3'-GCAGCAKKKACCGAG-5' | SEQ ID 15<br>SEQ ID 24 | 29.4 | The letter "K" represents 2,6-diamino-3-nitro-5-(1'-beta-D-2'-deoxyribofuranosyl)-pyridine.<br>The letter "S" represents 4-amino-N1-methyl-5-(1'-beta-D-2'-deoxyribofurarnsyl)-2(1H)-pyrimidinone. |
| 5'-CGTCGTTTTTGGCTC-3'<br>3'-GCAGCKAKAKCCGAG-5' | SEQ ID 3<br>SEQ ID 26 | 41.0 | The letter "K" represents 2,6-diamino-3-nitro-5-(1'-beta-D-2'-deoxyribofuranosyl)-pyridine. |
| 5'-CGTCGTTTTTGGCTC-3'<br>3'-GCAGCKKKKKCCGAG-5' | SEQ ID 3<br>SEQ ID 28 | 46.8 | The letter "K" represents 2,6-diamino-3-nitro-5-(1'-beta-D-2'-deoxyribofuranosyl)-pyridine. |

TABLE 3-continued

Mispairing in the skinny series gives less stable duplexes than the hydrogen bond matched skinny pairs, showing molecular recognition and its specificity.

| | | | |
|---|---|---|---|
| 5'-CGTCGTTSTTGGCTC-3'<br>3'-GCAGC*KKKKK*CCGAG-5' | SEQ ID 13<br>SEQ ID 28 | 39.0 | The letter "K" represents 2,6-diamino-3-nitro-5-(1'-beta-D-2'-deoxyribofuranosyl)-pyridine. The letter "S" represents 4-amino-N1-methyl-5-(1'-beta-D-2'-deoxyribofuranosyl)-2(1H)-pyrimidinone. |
| 5'-CGTCGTSSSTGGCTC-3'<br>3'-GCAGC*KKKKK*CCGAG-5' | SEQ ID 15<br>SEQ ID 28 | 30.6 | The letter "K" represents 2,6-diamino-3-nitro-5-(1'-beta-D-2'-deoxyribofuranosyl)-pyridine. The letter "S" represents 4-amino-N1-methyl-5-(1'-beta-D-2'-deoxyribofuranosyl)-2(1H)-pyrimidinone. |
| 5'-CGTCGSSSSSGGCTC-3'<br>3'-GCAGC*KKKKK*CCGAG-5' | SEQ ID 19<br>SEQ ID 28 | <20 | The letter "K" represents 2,6-diamino-3-nitro-5-(1'-beta-D-2'-deoxyribofuranosyl)-pyridine. The letter "S" represents 4-amino-N1-methyl-5-(1'-beta-D-2'-deoxyribofuranosyl)-2(1H)-pyrimidinone. |
| 5'-CGTCGTTTTTGGCTC-3'<br>3'-GCAGC*ZKZKZ*CCGAG-5' | SEQ ID 3<br>SEQ ID 41 | <20 | The letter "K" represents 2,6-diamino-3-nitro-5-(1'-beta-D-2'-deoxyribofuranosyl)-pyridine. The letter "Z" represents 6-amino-3(2'-deoxy-D-ribofuranosyl)-5-nitro-1H-pyridin-2-one. |
| 5'-CGTCGSTSTSGGCTC-3'<br>3'-GCAGC*ZKZKZ*CCGAG-5' | SEQ ID 17<br>SEQ ID 41 | 58.0 | The letter "K" represents 2,6-diamino-3-nitro-5-(1'-beta-D-2'-deoxyribofuranosyl)-pyridine. The letter "Z" represents 6-amino-3-(2'-deoxy-D-ribofuranosyl)-5-nitro-1H-pyridin-2-one. The letter "S" represents 4-amino-N1-methyl-5-(1'-beta-D-2'-deoxyribofuranosyl)-2(1H)-pyrimidinone. |
| 5'-CGTCGSSSSSGGCTC-3'<br>3'-GCAGC*ZKZKZ*CCGAG-5' | SEQ ID 19<br>SEQ ID 41 | 42.7 | The letter "K" represents 2,6-diamino-3-nitro-5-(1'-beta-D-2'-deoxyribofuranosyl)-pyridine. The letter "Z" represents 6-amino-3-(2'-deoxy-D-ribofuranosyl)-5-nitro-1H-pyridin-2-one. The letter "S" represents 4-amino-N1-methyl-5-(1'-beta-D-2'-deoxyribofuranosyl)-2(1H)-pyrimidinone. |
| 5'-CGTCGTTTTTGGCTC-3'<br>3'-GCAGCTTTTTCCGAG-5' | SEQ ID 3<br>SEQ ID 42 | <20 | These are all standard nucleotides. |
| 5'-CGTCGSSSSSGGCTC-3'<br>3'-GCAGCTTTTTCCGAG-5' | SEQ ID 19<br>SEQ ID 42 | <20 | The letter "S" represents 4-amino-N1-methyl-5-(1'-beta-D-2'-deoxyribofuranosyl)-2(1H)-pyrimidinone. |

TABLE 4

Comparing different implementations of the K hydrogen bonding pattern.

| | | | |
|---|---|---|---|
| 5'-CGTCGTTTTTGGCTC-3'<br>3'-GCAGCAA*K*AACCGAG-5' | SEQ ID 3<br>SEQ ID 30 | 45.9 | The letter "K" represents 2,4-diamino-5-(1'-beta-D-2'-deoxyribofuranosyl)-pyrimidine. |
| 5'-CGTCGTTTTTGGCTC-3'<br>3'-GCAGCAA*K*AACCGAG-5' | SEQ ID 3<br>SEQ ID 22 | 45.9 | The letter "K" represents 2,6-diamino-3-nitro-5-(1'-beta-D-2'-deoxyribofuranosyl)-pyridine. |
| 5'-CGTCGTTTTTGGCTC-3'<br>3'-GCAGCA*KKK*ACCGAG-5' | SEQ ID 3<br>SEQ ID 33 | 45.9 | The letter "K" represents 2,4-diamino-5-(1'-beta-D-2'-deoxyribofuranosyl)-pyrimidine. |

TABLE 4-continued

Comparing different implementations of the K hydrogen bonding pattern.

```
5'-CGTCGTTTTTGGCTC-3'      SEQ ID 3       48.0
3'-GCAGCAKKKACCGAG-5'      SEQ ID 24      The letter "K" represents 2,6-diamino-3-
                                          nitro-5-(1'-beta-D-2'-deoxyribofuranosyl)-
                                          pyridine.

5'-CGTCGTTTTTGGCTC-3'      SEQ ID 3       42.9
3'-GCAGCKAKAKCCGAG-5'      SEQ ID 36      The letter "K" represents 2,4-diamino-5-
                                          (1'-beta-D-2'-deoxyribofuranosyl)-
                                          pyrimidine.

5'-CGTCGTTTTTGGCTC-3'      SEQ ID 3       41.0
3'-GCAGCKAKAKCCGAG-5'      SEQ ID 26      The letter "K" represents 2,6-diamino-3-
                                          nitro-5(1'-beta-D-2'-deoxyribofuranosyl)-
                                          pyridine.

5'-CGTCGTTTTTGGCTC-3'      SEQ ID 3       41.0
3'-GCAGCKKKKKCCGAG-5'      SEQ ID 39      The letter "K" represents 2,4-diamino-5-
                                          (1'-beta-D-2'-deoxyribofuranosyl)-
                                          pyrimidine.

5'-CGTCGTTTTTGGCTC-3'      SEQ ID 3       46.8
3'-GCAGCKKKKKCCGAG-5'      SEQ ID 28      The letter "K" represents 2,6-diamino-3-
                                          nitro-5-(1'-beta-D-2'-deoxyribofuranosyl)-
                                          pyridine.

5'-CGTCGSSSSSGGCTC-3'      SEQ ID 19      <20
3'-GCAGCKKKKKCCGAG-5'      SEQ ID 39      The letter "K" represents 2,4-diamino-5-
                                          (1'-beta-D-2'-deoxyribofuranosyl)-
                                          pyrimidine.

5'-CGTCGSSSSSGGCTC-3'      SEQ ID 19      <20
3'-GCAGCKKKKKCCGAG-5'      SEQ ID 28      The letter "K" represents 2,6-diamino-3-
                                          nitro-5-(1'-beta-D-2'-deoxyribofuranosyl)-
                                          pyridine.
```

Example 5.4

Melting temperatures of duplexes consisting of only skinny base pairs, without Watson-Crick pairs at the ends of the species recognizing each other.

Measurements were made, as before, in 10 mM Na cacodylate (pH 6.8), 10 mM NaCl, and two micromolar of each oligonucleotide.

Watson-Crick Size Complementary Reference Sequences.

Duplex segment with molecular recognition involving 15 consecutive size complementary Watson-Crick pairs, as well known in the art. This serves as a reference sequence. D=diaminopurine. K=2,6-diamino-3-nitropyridine. Z is 6-amino-5-nitro-pyridin-2-one. X=7-deazaxanthosine. P=7-amino-9H-(imidazo[1,2-c]pyrimidin-5(1H)-one.

```
                                                  SEQ ID 43
OligoPyrimidine 1:    5'-KZZ TZS KTT KKS TST SEQ ID 44
OligoPurine 1:        3'-XPP DPB XDD XXB DBD
```

Melting temperature=60.9° C.

The letter "D" represents 2'-deoxy-2-aminoadenosine.

The letter "P" represents 7-amino-9-(1'-beta-D-2'-deoxyribofuranosyl)-imidazo[1,2-c]pyrimidin-5(1H)-one.

The letter "X" represents 2'-deoxy-7-deazaxanthosine.

The letter "B" represents 4-amino-3-hydro-7-(2-deoxy-beta-D-ribofuranosyl)-pyrrolo[2,3-d]pyrimidin-2-one.

The letter "Z" represents 6-amino-3-(2'-deoxy-D-ribofuranosyl)-5-nitro-1H-pyridin-2-one.

The letter "K" represents 2,6-diamino-3-nitro-5-(1'-beta-D-2'-deoxyribofuranosyl)-pyridine.

The letter "S" represents 4-amino-N1-methyl-5-(1'-beta-D-2'-deoxyribofuranosyl)-2(1H)-pyrimidinone.

```
                                                  SEQ ID 45
OligoPurine 2:        5'-DBB XBP DXX DDP XPX SEQ ID 46
OligoPyrimidine 2:    3'-TSS KSZ TKK TTZ KZK
```

Melting temperature=63.9° C.

The letter "D" represents 2'-deoxy-2-aminoadenosine.

The letter "P" represents 7-amino-9-(1'-beta-D-2'-deoxyribofuranosyl)-imidazo[1,2-c]pyrimidin-5(1H)-one.

The letter "X" represents 2'-deoxy-7-deazaxanthosine.

The letter "B" represents 4-amino-3-hydro-7-(2-deoxy-beta-D-ribofuranosyl)-pyrrolo[2,3-d]pyrimidin-2-one.

The letter "Z" represents 6-amino-3-(2'-deoxy-D-ribofuranosyl)-5-nitro-1H-pyridin-2-one.

The letter "K" represents 2,6-diamino-3-nitro-5-(1'-beta-D-2'-deoxyribofuranosyl)-pyridine.

The letter "S" represents 4-amino-N1-methyl-5-(1'-beta-D-2'-deoxyribofuranosyl)-2(1H)-pyrimidinone.

Standard-Watson-Crick: This Includes Weaker A:T Pairs.

```
                                                  SEQ ID 47
Standard Purine 1:      5'-AGA GAA AAA GGA GGA SEQ ID 48
Standard Pyrimidine 1:  3'-TCT CTT TTT CCT CCT
```

Melting temperature=36.5° C.

Standard-Watson-Crick: This includes weaker A:T pairs.

Standard Purine 2:      SEQ ID 49
                        5'-AGG AGG AAA AAG AGA Standard Pyrimidine 2:  SEQ ID 50
                        3'-TCC TCC TTT TTC TCT Melting temperature=34.8° C.
Duplex Segment with Molecular Recognition Involving 15 Consecutive "Skinny" Pairs.

This is the rule-based molecular recognition system of the current invention. Note that the thermodynamic stability of this duplex, as measured by its melting temperature, is only slightly below that of the reference sequences.

OligoPyrimidine 1:      SEQ ID 43
                        5'-KZZ TZS KTT KKS TST OligoPyrimidine 2:      SEQ ID 46
                        3'-TSS KSZ TKK TTZ KZK Melting temperature=58.3° C.

The letter "Z" represents 6-amino-3-(2'-deoxy-D-ribofuranosyl)-5-nitro-1H-pyridin-2-one.
The letter "K" represents 2,6-diamino-3-nitro-5-(1'-beta-D-2'-deoxyribofuranosyl)-pyridine.
The letter "S" represents 4-amino-N1-methyl-5-(1'-beta-D-2'-deoxyribofuranosyl)-2(1H)-pyrimidinone.

Watson-Crick with Mispairs

OligoPyrimidine 1:      SEQ ID 43
                        5'-KZZ TZS KTT KKS TST OligoPurine 2:          SEQ ID 45
                        5'-DBB XBP DXX DDP XPX Melting temperature<20° C.
The letter "D" represents 2'-deoxy-2-aminoadenosine.
The letter "P" represents 7-amino-9-(1'-beta-D-2'-deoxyribofuranosyl)-imidazo[1,2-c]pyrimidin-5(1H)-one.
The letter "X" represents 2'-deoxy-7-deazaxanthosine.
The letter "B" represents 4-amino-3-hydro-7-(2-deoxy-beta-D-ribofuranosyl)-pyrrolo[2,3-d]pyrimidin-2-one.
The letter "Z" represents 6-amino-3-(2'-deoxy-D-ribofuranosyl)-5-nitro-1H-pyridin-2-one.
The letter "K" represents 2,6-diamino-3-nitro-5-(1'-beta-D-2'-deoxyribofuranosyl)-pyridine.
The letter "S" represents 4-amino-N1-methyl-5-(1'-beta-D-2'-deoxyribofuranosyl)-2(1H)-pyrimidinone.

OligoPyrimidine 2:      SEQ ID 46
                        5'-KZK ZTT KKT ZSK SST OligoPurine 1:          SEQ ID 44
                        5'-DBD BXX DDX BPD PPX Melting temperature<20° C.
The letter "D" represents 2'-deoxy-2-aminoadenosine.
The letter "P" represents 7-amino-9-(1'-beta-D-2'-deoxyribofuranosyl)-imidazo[1,2-c]pyrimidin-5(1H)-one.
The letter "X" represents 2'-deoxy-7-deazaxanthosine.
The letter "B" represents 4-amino-3-hydro-7-(2-deoxy-beta-D-ribofuranosyl)-pyrrolo[2,3-d]pyrimidin-2-one.
The letter "Z" represents 6-amino-3-(2'-deoxy-D-ribofuranosyl)-5-nitro-1H-pyridin-2-one.
The letter "K" represents 2,6-diamino-3-nitro-5-(1'-beta-D-2'-deoxyribofuranosyl)-pyridine.
The letter "S" represents 4-amino-N1-methyl-5-(1'-beta-D-2'-deoxyribofuranosyl)-2(1H)-pyrimidinone.

Single Stranded Melting Temperatures
These show no folding.

Fatty1-15:              SEQ ID 44
                        5'-DBD BXX DDX BPD PPX The letter "D" represents 2'-deoxy-2-aminoadenosine.
The letter "P" represents 7-amino-9-(1'-beta-D-2'-deoxyribofuranosyl)-imidazo[1,2-c]pyrimidin-5(1H)-one.
The letter "X" represents 2'-deoxy-7-deazaxanthosine.
The letter "B" represents 4-amino-3-hydro-7-(2-deoxy-beta-D-ribofuranosyl)-pyrrolo[2,3-d]pyrimidin-2-one.
Melting temperature<20° C.

Fatty2-15:              SEQ ID 45
                        5'-DBB XBP DXX DDP XPX The letter "D" represents 2'-deoxy-2-aminoadenosine.
The letter "P" represents 7-amino-9-(1'-beta-D-2'-deoxyribofuranosyl)-imidazo[1,2-c]pyrimidin-5(1H)-one.
The letter "X" represents 2'-deoxy-7-deazaxanthosine.
The letter "B" represents 4-amino-3-hydro-7-(2-deoxy-beta-D-ribofuranosyl)-pyrrolo[2,3-d]pyrimidin-2-one.
Melting temperature<20° C.

Skinny1-15:             SEQ ID 43
                        5'-KZZ TZS KTT KKS TST The letter "Z" represents 6-amino-3-(2'-deoxy)-D-ribofuranosyl)-5-nitro-1H-pyridin-2-one.
The letter "K" represents 2,6-diamino-3-nitro-5-(1'-beta-D-2'-deoxyribofuranosyl)-pyridine.
The letter "S" represents 4-amino-N1-methyl-5-(1'-beta-D-2'-deoxyribofuranosyl)-2(1H)-pyrimidinone.
Melting temperature<20° C.

Skinny2-15:             SEQ ID 46
                        5'-KZK ZTT KKT ZSK SST Melting temperature<20° C. IDC-39 DNA The letter "Z" represents 6-amino-3-(2'-deoxy)-D-ribofuranosyl)-5-nitro-1H-pyridin-2-one.
The letter "K" represents 2,6-diamino-3-nitro-5-(1'-beta-D-2'-deoxyribofuranosyl)-pyridine.
The letter "S" represents 4-amino-N1-methyl-5-(1'-beta-D-2'-deoxyribofuranosyl)-2(1H)-pyrimidinone.

Example 6. Measurement of Melting Temperatures

All Skinny
AEGIS all skinny geometry

SEQ ID 43
        5'-KZZ TZS KTT KKS TST

SEQ ID 46
        3'-TSS KSZ TKK TTZ KZK

The $T_m$ is 58.3±0.9° C.
The letter "Z" represents 6-amino-3-(2'-deoxy-D-ribofuranosyl)-5-nitro-1H-pyridin-2-one.
The letter "K" represents 2,6-diamino-3-nitro-5-(1'-beta-D-2'-deoxyribofuranosyl)-pyridine.
The letter "S" represents 4-amino-N1-methyl-5-(1'-beta-D-2'-deoxyribofuranosyl)-2(1H)-pyrimidinone.

Example 7. Crystal Structures

These biophysical measurement raise the question: Do skinny and fat pairs actually adopt their designed "edge on" structure or an unintended structure? To answer this question, self-complementary 16-mers were made with four skinny pairs:

5'-CTTATAKKTTTATAAG-3' SEQ ID 55 inserted between flanking Watson-Crick standard pairs. These were then crystallized in the host-guest system of Georgiadis [Cot6, M. L.; Yohannan, S. J.; Georgiadis, M. M. *Acta Crystal. Section D: Biol. Crystallography* 2000, 56, 1120-1131. Georgiadis, M. M.; Singh, I.; Kellett, W. F.; Hoshika, S.; Benner, S. A.; Richards, N. G. J. *J. Am. Chem. Soc.* 2015, 137, 6947-6955]. Here, the host is the N-terminal fragment of Moloney murine leukemia virus reverse transcriptase; the guest is the DNA duplex, which binds to the host via contacting only the three pairs at each end. The result is a complex with two hosts bound to a single guest in which the central ten pairs of the guest DNA are free from interactions with the host protein, and free to adopt sequence-dependent local structure. Three structures for the three host-guest complexes were determined at 2.0 Å (PDB ID 6B1S), 1.69 Å (PDB ID 6B1R), and 1.9 Å (PDB 6B1Q) resolution. These three structures leave no doubt that the skinny and fat pairs form as expected, giving their own "double helices". In each case, they exploit all three of their expected hydrogen bonds. Overall, the skinny pairs are accurately characterized as "skinny", joined by three hydrogen bonds in pairs having anti-base sugar geometries. The skinny central region is classified as neither A- nor B-form DNA; the flanking portions are B-form. The skinny regions of the duplex have 10.7 bp/turn, somewhat tighter than standard duplexes. The minor groove width of the skinny section is 11.2 Å, between that found in A:T duplexes (9.6 Å) and that found in G:C duplexes (12.3 Å). The major groove width (19.2 Å) in the skinny structure is the same as in A:T duplexes, which are both larger than the groove in G:C duplexes (17.7 Å). The difference in the width of the minor and major grooves in skinny DNA (7.0 Å) is also between that of A:T DNA (9.6 Å) and that of G:C DNA (5.4 Å). The C1'-C1' distance for the skinny pairs is on average 8.6 Å as compared to 10.4-10.5 Å for A:T or G:C pairs.

Example 8. Priming of Polymerase Synthesis Using Fat and Skinny Priming Duplexes Polymerases are not expected to synthesize skinny or fat duplex DNA. Indeed, the one environment where hydrophobic pairs lacking inter-base hydrogen bonding might work is in the active sites of polymerases, which appear to enforce an edge-on size complementarity, a geometry that they do not intrinsically adopt because they lack the directionality imposed by hydrogen bonding. Instead, we asked whether any DNA polymerase could initiate polymerization from skinny or fat primer-template complexes. Six primer template complexes (FIG. 10) were used to test a panel of DNA polymerases. Surprisingly, Klenow fragment of DNA polymerase I can use a skinny primer-template complex to initiate the synthesis of duplex Watson-Crick DNA. Initiation was less efficient from the skinny duplex than the standard duplex; in a ten-minute incubation, only 15% of the skinny primer-template is extended, while 90% of the standard duplex primer is.

This exemplifies a process for extending a primer using a polymerase, preferably the Klenow fragment of DNA polymerase 1 or the corresponding fragment of Taq polymerase 1 (the "Stoffel fragment", derived from the DNA polymerase from *Thermus aquaticus*), where the process comprises contacting a polymerase with a duplex between a primer that can form skinny pairs at its 3'-end (at least 3 skinny pairs, more preferably 5 or more skinny pairs), and a template oligonucleotide. For this, the template must have within itself a segment of DNA comprising entirely nucleotides able to form skinny pairs with the 3'-end of the template oligonucleotide. The template segment 3'-distal to the first segment can comprise any nucleotides; this is the segment that the polymerase will copy. Again, the primer and the primer-binding region on the template can carry tags, as disclosed above, including 5'-end modifications well known in the art.

What is claimed is:

1. A folded oligonucleotide strand, wherein said strand contains a first part and a second part, each part consisting solely of three or more consecutive nucleotides independently selected from the group consisting of

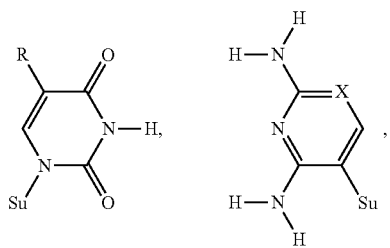

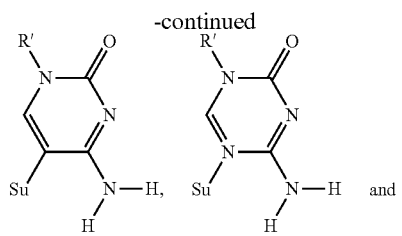

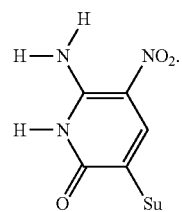

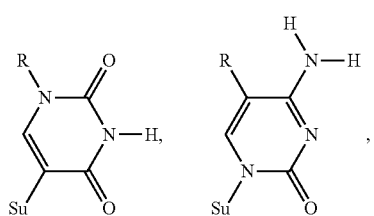

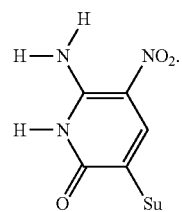

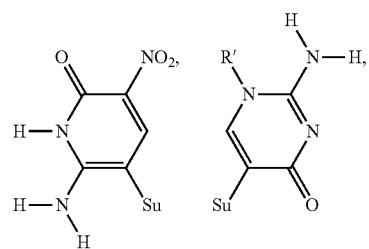

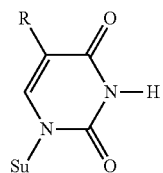

wherein Su indicates the point of attachment of said heterocycle to a sugar of said first or second oligonucleotide, R' is $CH_3$, alkyl, alkenyl, alkynyl, or alkyl, alkenyl, or alkynyl carrying a functional group, wherein R is H, $CH_3$, alkyl, alkenyl, or alkynyl, or functionalized alkyl, alkenyl, or alkynyl, and X is N or C—$NO_2$, wherein said parts form an antiparallel duplex in which said segments are joined by skinny pairs, wherein is paired with
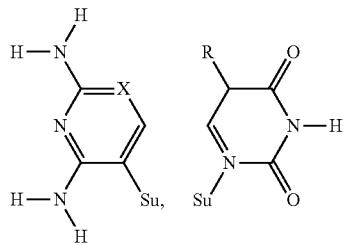
is paired with
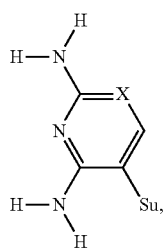
is paired with
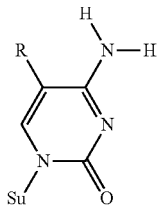
is paired with
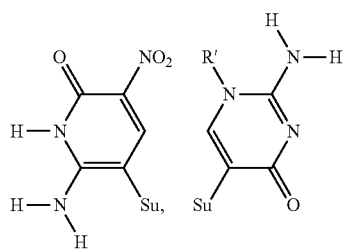
is paired with
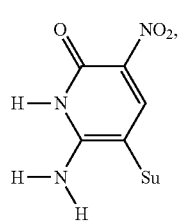
is paired with
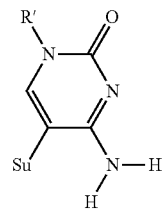
is paired with
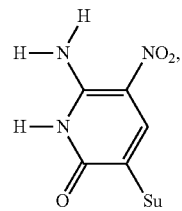
and
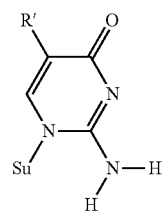
is paired with
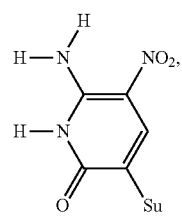
and wherein said duplex region comprises at least three such pairs, and wherein said oligonucleotide outside of said parts comprises nucleotides independently selected from the group consisting of
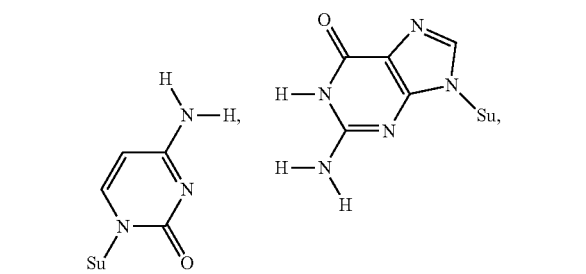

-continued
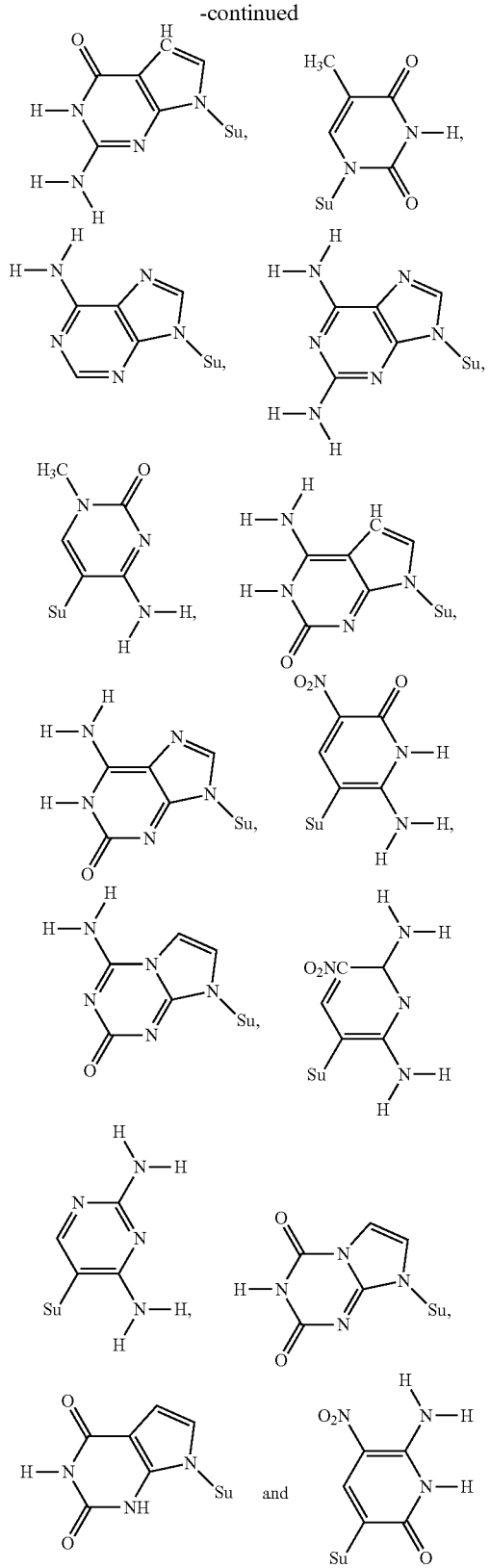
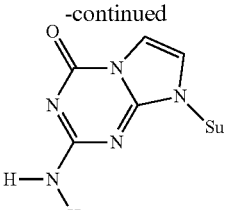
wherein Su indicates the point of attachment of the indicated heterocycle to the sugar of the oligonucleotide backbone.
2. The composition of claim 1, wherein said functional group is an amino group or a thiol group.
3. The composition of claim 1, wherein said nucleotide in said parts are independently selected from the group consisting of
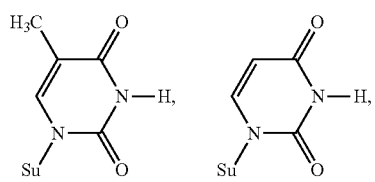
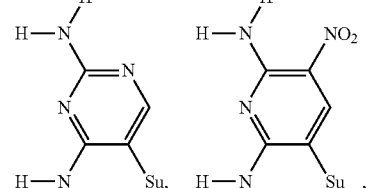
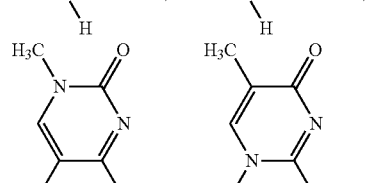
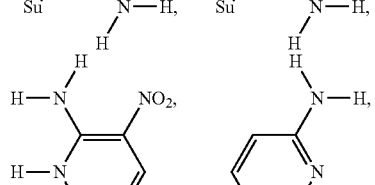
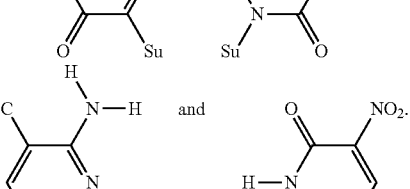
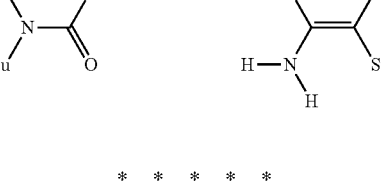
* * * * *